United States Patent [19]

Yamamoto et al.

[11] Patent Number: 5,270,339
[45] Date of Patent: Dec. 14, 1993

[54] PHENOXYBENZENE DERIVATIVE

[75] Inventors: Kozo Yamamoto, Takasago; Yoshihide Fuse, Himeji; Hideyuki Kishida, Kakogawa; Naoko Yasuhara, Takasago; Toshiaki Miwa, Kobe; Ikuo Katsumi, Kobe; Takayoshi Hidaka, Kobe, all of Japan

[73] Assignee: Kanagafuchi Kagaku Kogyo Kabushiki Kaisha, Osaka, Japan

[21] Appl. No.: 938,164

[22] PCT Filed: Apr. 2, 1992

[86] PCT No.: PCT/JP92/00410
§ 371 Date: Dec. 3, 1992
§ 102(e) Date: Dec. 3, 1992

[87] PCT Pub. No.: WO92/17447
PCT Pub. Date: Oct. 15, 1992

[30] Foreign Application Priority Data

Apr. 5, 1991 [JP] Japan .................. 3-73065
Jun. 3, 1991 [JP] Japan .................. 3-131122
Jul. 10, 1991 [JP] Japan .................. 3-170042

[51] Int. Cl.$^5$ .............. C07D 207/08; C07D 207/06; C07D 207/20; C07D 207/24
[52] U.S. Cl. .............. 514/408; 514/422; 514/423; 514/424; 514/425; 514/429; 548/400; 548/517; 548/524; 548/531; 548/538; 548/539; 548/540; 548/542; 548/543; 548/545; 548/550; 548/551
[58] Field of Search .............. 548/543, 542, 538, 539, 548/540, 545, 550, 551, 524, 400, 517, 531; 514/424, 408, 425, 423, 422, 429

[56] References Cited

U.S. PATENT DOCUMENTS 3,732,247  5/1970  Helsley et al. .............. 260/326

FOREIGN PATENT DOCUMENTS 61-218571  9/1986  Japan .

OTHER PUBLICATIONS

Vosmer et al, E. M. "Action of the Antidepressant Pridefine (AHR-1118) on Biogenic Amines in the Rat Brain", *Biochemical Pharmacology*, vol. 29, pp. 2557–2562 (1980).

Primary Examiner—Mary C. Lee
Assistant Examiner—Joseph K. McKane
Attorney, Agent, or Firm—Armstrong, Westerman, Hattori, McLeland, & Naughton

[57] ABSTRACT

There are described a phenoxybenzene derivative having the formula (I):

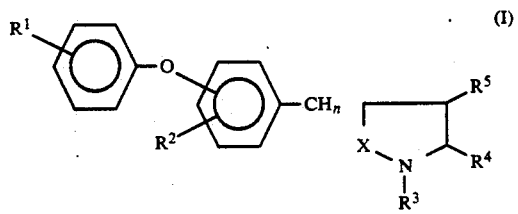

wherein $R^1$ is hydrogen atom; an alkyl group having 1 to 3 carbon atoms; $-OR^6$ or a halogen atom,
$R^2$ is hydrogen atom, nitro group or amino group,
$R^3$ is hydrogen atom, an alkyl group having 1 to 8 carbon atoms, a cycloalkyl group having 3 to 5 carbon atoms, allyl group, vinyl group or $-(CH_2)n^1R^7$
$R^4$ is hydrogen atom, an alkyl group having 1 to 3 carbon atoms or $-(CH_2)n^3R^{25}$
$R^5$ hydrogen atom; an alkyl group having 1 to 3 carbon atoms; or phenyl group,
X is $$-\overset{\overset{Y}{\|}}{C}-$$

wherein Y is oxygen atom or sulfur atom; or $-CHR^{27}-$ and
line ==== means a single bond or a double bond provided that n is 2 in case that the line ==== means a single bond and n is 1 in case that the line ==== means a double bond, or
a pharmacologically acceptable salt thereof,
a cognition enhancer comprising the same as an effective ingredient and
an antidepressant comprising the same as an effective ingredient.

3 Claims, No Drawings

PHENOXYBENZENE DERIVATIVE

TECHNICAL FIELD

The present invention is useful in the medicinal field. The present invention relates to a novel phenoxybenzene derivative and a salt thereof, which has cognition enhancing activity and antidepressive activity, and a cognition enhancer comprising the same as an effective ingredient and an antidepressant comprising the same as an effective ingredient.

BACKGROUND ART

With increasing a population of aged generation, dementia is occupying large weight in care of the aged. Although many medicines have been developed in order to improve various types of dementia such as dysmnesia, they are not fully enough in the points of efficacy, persistence and side effect.

For example, the function of cholinergic nervous system in hippocampus, amygdala and cerebral cortex is depressed in brains of patients of Alzheimer's disease (Pope et al., Trans. Am. Neurol. Assoc., 89, 15 (1964), Bowen et al., Brain, 266, 558 (1976) and Davies et al., Lancet, ii, 1043 (1976)). The above-mentioned is considered to be firmly concerned with nosogenesis of the impairment of memorization or memory which is main symptom of Alzheimer's disease (Whitehouse et al., Science, 215, 1237 (1982)). Therefore, there is a possibility that these disturbances are improved by potentiating cholinergic nervous system. However, agonists of muscarinic cholinergic receptor which have been used up to date have high toxicity in spite of showing efficacy and therefore have not been practically used (Wettsein et al., Psychopharmacology, 84, 572 (1984) and Hollander et al., Biol. Psychiatry, 22, 1067 (1987)).

On the other hand, in a highly information-oriented society, there increase diseases due to mental repression. As one of such diseases, depression can be exemplified. Although there are many medicaments for depression, they are not fully satisfiable in the points of fast-acting property and side effect.

So, more effective and safe medicaments are required for the above-mentioned diseases.

DISCLOSURE OF THE INVENTION

As a result of continuous effort and detailed investigation of the present inventors in view of the above-mentioned actual circumstances, it has now been found that a novel phenoxybenzene derivative and a salt thereof show anti-amnesic activity by oral administration in animal experiments such as experimental amnesic mice, that the above-mentioned compounds potentiate central chlolinergic neural function as a characteristic of anti-amnesic activity by acting on muscarinic chlorinergic receptors, that the above-mentioned compounds show potent antidepressive activity by both oral and parenteral administeration in a forced swimming test with rats and that toxicity of the above-mentioned compounds is low. Therefore the above-mentioned compounds have been found to be useful as a cognition enhancer and an antidepressant, and thus the present invention has been accomplished.

That is, the present invention relates to

① a phenoxybenzene derivative having the formula (I):

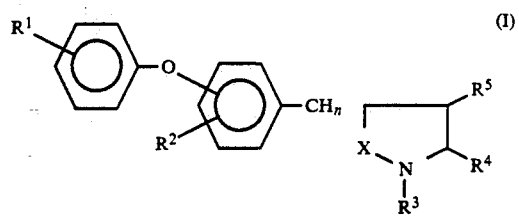

wherein $R^1$ is hydrogen atom; an alkyl group having 1 to 3 carbon atoms; —$OR^6$ wherein $R^6$ is hydrogen atom or an alkyl group having 1 to 3 carbon atoms; or a halogen atom, $R^2$ is hydrogen atom, nitro group or amino group, $R^3$ is hydrogen atom, an alkyl group having 1 to 8 carbon atoms, a cycloalkyl group having 3 to 5 carbon atoms, allyl group, vinyl group or —$(CH_2)n^1R^7$ wherein $R^7$ is —$OR^8$ wherein $R^8$ is hydrogen atom, an alkyl group having 1-3 carbon atoms or tetrahydropyranyl group, a halogen atom, —$COOR^9$ wherein $R^9$ is hydrogen atom or an alkyl group having 1 to 3 carbon atoms,

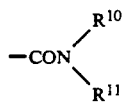

wherein $R^{10}$ and $R^{11}$ are independently hydrogen atom; an alkyl group having 1-3 carbon atoms;

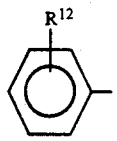

wherein $R^{12}$ is hydrogen atom or —$OR^{13}$ wherein $R^{13}$ is hydrogen atom or an alkyl group having 1 to 3 carbon atoms; or

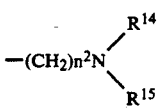

wherein $R^{14}$ and $R^{15}$ are independently hydrogen atom or an alkyl group having 1 to 3 carbon atoms and $n^2$ is an integer of 1 to 3, cyano group,

wherein $R^{16}$ and $R^{17}$ are independently hydrogen atom or an alkyl group having 1 to 3 carbon atoms, —$COR^{18}$ wherein $R^{18}$ is an alkyl group having 1-3 carbon atoms;

wherein $R^{19}$ is hydrogen atom or $-OR^{20}$ wherein $R^{20}$ is hydrogen atom or an alkyl group having 1 to 3 carbon atoms; or

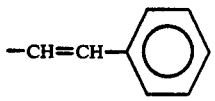

or a phenyl group having the formula

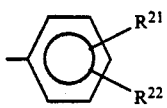

wherein $R^{21}$ and $R^{22}$ are independently hydrogen atom; $-OR^{23}$ and $-OR^{24}$ wherein $R^{23}$ and $R^{24}$ are independently hydrogen atom or an alkyl group having 1 to 3 carbon atoms; or a halogen atom and $n^1$ is an integer of 0 to 4, $R^4$ is hydrogen atom, an alkyl group having 1 to 3 carbon atoms or $-(CH_2)n^3R^{25}$ wherein $R^{25}$ is $-OR^{26}$ wherein $R^{26}$ is hydrogen atom or an alkyl group having 1-3 carbon atoms; or pyrrolidyl group, and $n^3$ is an integer of 0 to 3, $R^5$ is hydrogen atom; an alkyl group having 1 to 3 carbon atoms; or phenyl group, X is

wherein Y is oxygen atom or sulfur atom; or $-CHR^{27}-$ wherein $R^{27}$ is hydrogen atom or an alkyl group having 1 to 5 carbon atoms and line ==== means a single bond or a double bond provided that n is 2 in case that the line ==== means a single bond and n is 1 in case that the line ==== means a double bond, or a pharmacologically acceptable salt thereof (2) A cognition enhancer comprising as an effective ingredient the above-mentioned phenoxybenzene derivative or a pharmacologically acceptable salt thereof and (3) An antidepressant comprising as an effective ingredient the above-mentioned phenoxybenzene derivative or a pharmacologically acceptable salt thereof.

In the compound of the present invention having the formula (I), an alkyl group means a straight or branched chain hydrocarbon.

The compound of the present invention can be synthesized by, for example, the following processes.

(1) The compound having the formula (Ia) (the line ==== means a double bond in the formula (I):

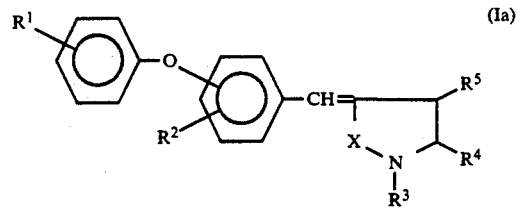

wherein $R^1$, $R^2$, $R^3$, $R^4$, $R^5$ and X are the same as defined above, can be synthesized by binding a benzaldehyde derivative having the formula (II):

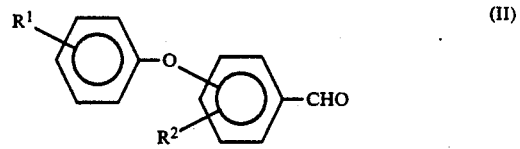

wherein $R^1$ and $R^2$ are the same as defined above and a compound having the formula (III):

wherein $R^3$, $R^4$, $R^5$ and X are the same as defined above without a catalyst or with a catalyst such as an acid or a base according to H. Zimmer's process (J. Heterocyclic Chem., 2, P 171 (1965)).

As an acid usable for the catalyst, there are, for example, a protonic acid such as sulfuric acid, benzenesulfonic acid or p-toluenesulfonic acid; a Lewis acid such as boron trifluoride and the like. As a base usable for a catalyst, there are, for example, an organic base such as monoethanolamine, pyridine or 1,8-diazabicyclo[5,4,-0]undec-7-ene, a hydroxide of alkaline metal such as sodium hydroxide or potassium hydroxide, an alkaline metal salt of organic acid such as sodium acetate or potassium acetate, an amide of alkaline metal such as lithium diisopropylamide, an alcoholate of alkaline metal such as sodium methylate or sodium ethylate, a hydride of alkaline metal such as sodium hydride or potassium hydride and the like.

(2) The compound having the formula (Ia) can be synthesized by reacting a benzaldehyde derivative having the above-mentioned formula (II) and a ylide having the formula (IV):

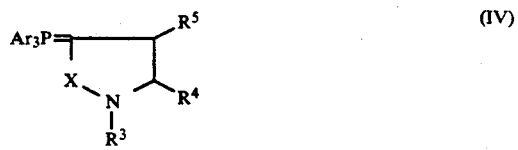

wherein Ar is an aryl group, $R^3$, $R^4$, $R^5$ and X are the same as above defined according to the process of H. Wamhoff et al. (Synthesis, P 331 (1976)). This synthesis process utilizes the so-called Wittig reaction. As a ylide to be reacted with the above-mentioned formula (II), a ylide derived from a trialkylphosphine or a triarylarsine can be also used besides the compound having the above-mentioned formula (IV).

(3) Among the compounds having the formula (Ia), the compound (Ia) wherein X is

can be obtained by reacting a benzaldehyde derivative having the formula (II) and a 3-carboxy-2-pyrrolidone derivative having the formula (V):

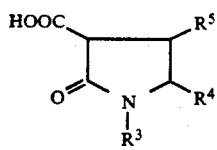

wherein $R^3$, $R^4$ and $R^5$ are the same as defined above in the presence of a basic catalyst, for example, an organic base such as pyrrolidine or piperidine, a hydride of alkaline metal such as lithium hydride or sodium hydride, a carbonate of alkaline metal such as sodium carbonate or potassium carbonate and the like.

(4) Among the compounds having the formula (Ia), the compound (Ia) wherein X is

can be also obtained by reacting a compound having the formula (VI):

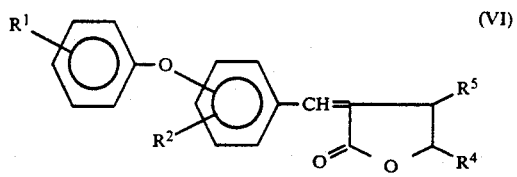

wherein $R^1$, $R^2$, $R^4$ and $R^5$ are the same as above defined and a compound having the formula (VII):

$H_2N—R^3$ (VII)

wherein $R^3$ is the same as above defined according to the process of F. B. Zienty et al. (J. Am. Chem. Soc., 69, P 715 (1947)).

When $R^3$ is —$COR^{18}$ wherein $R^{18}$ is the same as above defined and an acyl group remains at nitrogen atom of pyrrolidone group in the compound obtained in the above mentioned (1) to (4), the elimination can be carried out by the hydrolysis with a base such as a hydroxide of alkaline metal e.g. sodium hydroxide to give a compound wherein $R^3$ is hydrogen atom.

(5) On the other hand, the compound having the formula (Ib) (the line ==== means a single bond in the formula (I):

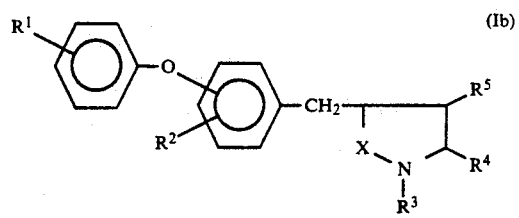

wherein $R^1$, $R^2$, $R^3$, $R^4$, $R^5$ and X are the same as above defined can be obtained by saturating the double bond of the compound having the formula (Ia) according to a usual reduction process such as a catalytic reduction process using a metal catalyst such as palladium or nickel.

(6) The compound having the formula (I) can be also obtained by binding the compound (I) wherein $R^3$ is H:

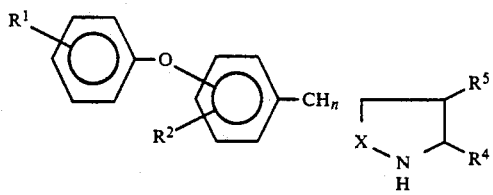

wherein $R^1$, $R^2$, $R^4$, $R^5$ and X are the same as above defined and a compound having the formula (VIII):

$Z^1R^3$ (VIII)

wherein $R^3$ is the same as above defined and $Z^1$ is a halogen atom, hydroxyl group, mesyl group or tosyl group without a catalyst or with a base as a catalyst, otherwise with a condensing agent such as dicyclohexylcarbodiimide.

Among the compounds having the formula (I), the compound (I) wherein $R^3$ is —$COR^{18}$ wherein $R^{18}$ is the same as above defined can be synthesized by reacting the compound (I) wherein $R^3$ is H and an anhydride of an acid having the formula (IX):

$R^{18}COOH$ (IX)

wherein $R^{18}$ is the same as above defined or the mixed acid anhydride with acetic acid, without a catalyst or with a base as a catalyst.

As the base usable for a catalyst, there are, for example, an organic base such as monoethanolamine, pyridine or 1,8-diazabicyclo[5,4,0]undec-7ene, an hydroxide of alkaline metal such as sodium hydroxide or potassium hydroxide, an alkaline metal salt of organic acid such as sodium acetate or potassium acetate, an amide of alkaline metal such as lithium diisopropylamide, an alcoholate of alkaline metal such as sodium methylate or sodium ethylate, a hydride of alkaline metal such as sodium hydride or potassium hydride and the like.

(7) Among the compound having the formula (I), the compound (I) wherein $R^3$ is —$(CH_2)n^1R^7$ and $R^7$ is —$OR^8$ wherein $R^8$ is tetrahydropyranyl group can be converted into the compound (I) wherein $R^8$ is hydrogen atom according to a usual process. The compound (I) wherein $R^3$ is —$(CH_2)n^1R^7$, $R^7$ is —$COOR^9$ and $R^9$ is an alkyl group having 1 to 3 carbon atoms can be also converted into the compound (I) wherein $R^9$ is H according to a usual hydrolysis process. The compound (I) wherein $R^9$ is H can be used as it is or as an acid chloride which is obtained by using a generally usable halogenating agent such as phosphorus pentachloride or thionyl chloride, for reacting with a compound having the formula (X):

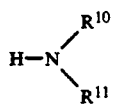 (X)

wherein $R^{10}$ and $R^{11}$ are the same as above defined or hexamethyldisilazane without a catalyst or, if necessary, with a base catalyst or a condensing agent such as DCC(dicyclohexylcarbodiimide) in order to convert into the compound (I) wherein $R^3$ is $-(CH_2)n^1R^7$ and $R^7$ is

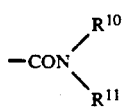

wherein $R^{10}$ and $R^{11}$ are the same as above defined.

As a base catalyst optionally used herein, there are, for example, an organic base such as triethylamine or pyridine, an alkaline metal salt of organic acid such as sodium acetate, a hydroxide of alkaline metal such as sodium hydroxide, a carbonate of alkaline metal such as sodium carbonate and the like.

(8) Among the compound having the formula (I), the compound (I) wherein $R^3$ is $-COR^{18}$ can be reduced with a usual reducing agent such as LiAl $H_4$ (lithium aluminum hydride) to be converted into the compound (I) wherein $R^3$ is an alkyl group.

(9) The compound having the formula (I) wherein X is methylene group:

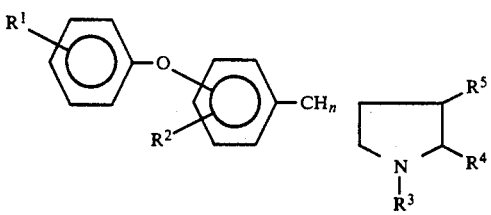

wherein $R^1$, $R^2$, $R^3$, $R^4$ and $R^5$ are the same as above defined can be obtained from the compound (I) wherein X is

wherein Y is the same as above defined, by the reduction with a usual reducing agent such as a complexed compound of metal hydride e.g., lithium aluminum hydride or sodium borohydride, or by the catalytic reduction with a catalyst such as palladium, platinum or nickel.

(10) The compound having the formula (Ia) wherein X is $-CHR^{27}-$ and $R^3$ is H:

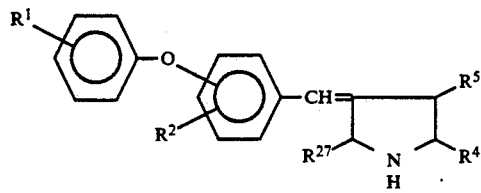

wherein $R^1$, $R^2$, $R^4$, $R^5$ and $R^{27}$ are the same as above defined can be obtained by reacting the benzaldehyde having the formula (II) and pyrroline trimer:

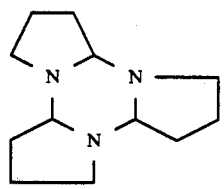

thereby a pyrroline derivative being synthesized, followed by reacting with a compound having the formula (XI):

$$R^{27}Z^2 \qquad (XI)$$

wherein $R^{27}$ is the same as above defined, $Z^2$ is a metal or a halogenated metal such as Li or MgBr. Thus obtained compound, of course, can be modified at a nitrogen atom of pyrrolidine by the above mentioned process.

(11) Among the compound having the formula (I), the compound (I) wherein $R^2$ is amino group can be obtained by reducing the compound (I) wherein $R^2$ is nitro group according to a usual reduction process, for example, Clemmensen reduction which uses an acid such as chloric acid, sulfuric acid or acetic acid and a metal or a salt of metal such as iron, tin or tin chloride.

Thus obtained compound of the present invention can be used not only as a cognition enhancer or an antidepressant, but also as an intermediate in the synthesis of various compounds.

BEST MODE FOR CARRYING OUT THE INVENTION

There are exemplified the representatives of the compounds having the formula (I) obtained according to the present invention in Table 1.

TABLE 1

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 1 | 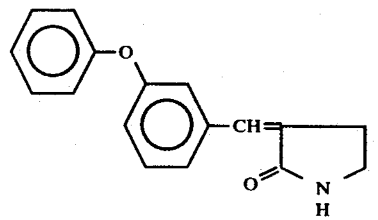 | C₁₇H₁₅NO₂ (265.30) | 132~135 | 77.18 | 76.96 | 5.42 | 5.70 | 5.56 | 5.28 |
| 2 | 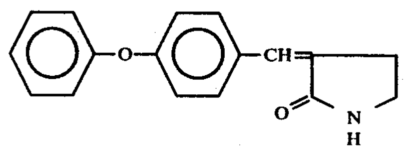 | C₁₇H₁₅NO₂ (265.30) | 200~203 | 76.60 | 76.96 | 5.34 | 5.70 | 5.65 | 5.28 |
| 3 | 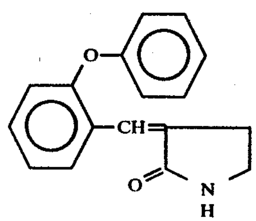 | C₁₇H₁₅NO₂ (265.30) | 202~204 | 77.18 | 76.96 | 5.57 | 5.70 | 5.56 | 5.28 |
| 4 | 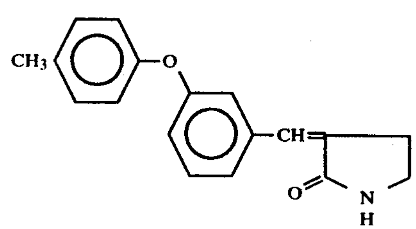 | C₁₈H₁₇NO₂ (279.32) | 156~157 | 77.21 | 77.39 | 6.00 | 6.13 | 5.37 | 5.01 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 5 | [structure with CH₃O-phenyl-O-phenyl-CH-pyrrolidinone] | C₁₈H₁₇NO₃ (295.32) | 151~152 | 72.98 | 73.20 | 5.68 | 5.80 | 5.02 | 4.74 |
| 6 | [structure with Cl-phenyl-O-phenyl-CH-pyrrolidinone] | C₁₇H₁₄NO₂Cl (299.76) | 139~141 | 68.39 | 68.12 | 4.50 | 4.71 | 4.99 | 4.67 |
| 7 | [structure with NO₂-phenyl-O-phenyl-CH-pyrrolidinone] | C₁₇H₁₄NO₂O₄ (310.30) | 155~160 | 65.44 | 65.80 | 4.86 | 4.55 | 8.66 | 9.03 |
| 8 | [structure with NH₂·HCl-phenyl-O-phenyl-CH-pyrrolidinone] | C₁₇H₁₇N₂O₂Cl (316.74) | 250~253 | 64.07 | 64.46 | 5.12 | 5.41 | 9.21 | 8.84 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 9 | phenoxyphenyl-CH=pyrrolidinone-N-CH₃ | C₁₈H₁₇NO₂ (279.32) | 140~142 | 77.21 | 77.39 | 6.23 | 6.13 | 4.89 | 5.01 |
| 10 | phenoxyphenyl-CH=pyrrolidinone-N-CH₂CH₃ | C₁₉H₁₉NO₂ (293.35) | 95~96 | 77.43 | 77.79 | 6.75 | 6.53 | 4.41 | 4.77 |
| 11 | phenoxyphenyl-CH=pyrrolidinone-N-(CH₂)₂CH₃ | C₂₀H₂₁NO₂ (307.38) | 57~59 | 78.23 | 78.14 | 6.98 | 6.89 | 4.32 | 4.56 |
| 12 | phenoxyphenyl-CH=pyrrolidinone-N-(CH₂)₃CH₃ | C₂₁H₂₃NO₂ (321.40) | 63~67 | 78.83 | 76.47 | 7.04 | 7.21 | 4.68 | 4.36 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 13 | [3-phenoxybenzylidene pyrrolidinone with N-(CH₂)₅CH₃] | C₂₃H₂₇NO₂ (349.45) | 74~78 | 78.69 | 79.05 | 7.51 | 7.79 | 4.37 | 4.01 |
| 14 | [4-phenoxybenzylidene pyrrolidinone with N-CH₂CH₃] | C₁₉H₁₉NO₂ (293.35) | 110~112 | 77.91 | 77.79 | 6.65 | 6.53 | 4.49 | 4.77 |
| 15 | [3-(4-methylphenoxy)benzylidene pyrrolidinone with N-CH₂CH₃] | C₂₀H₂₁NO₂ (307.38) | 86~88 | 78.41 | 78.14 | 6.66 | 6.89 | 4.89 | 4.56 |
| 16 | [3-phenoxybenzylidene pyrrolidinone with N-CH(CH₃)₂] | C₂₀H₂₁NO₂ (307.38) | 67~70 | 78.47 | 78.14 | 6.63 | 6.89 | 4.23 | 4.56 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 17 | (3-phenoxyphenyl)-CH=/pyrrolidinone N-cyclopropyl | $C_{20}H_{19}NO_2$ (305.36) | 104~105 | 78.47 | 78.66 | 6.21 | 6.27 | 4.78 | 4.59 |
| 18 | (4-phenoxyphenyl)-CH=/pyrrolidine N-CH$_2$CH$_3$ | $C_{19}H_{21}NO$ (279.37) | Oil | 81.97 | 81.68 | 7.23 | 7.58 | 5.33 | 5.01 |
| 19 | (3-phenoxy-methylphenyl)-CH=/pyrrolidine N-CH$_2$CH$_3$ | $C_{20}H_{23}NO$ (293.39) | Oil | 81.52 | 81.87 | 8.01 | 7.90 | 5.15 | 4.77 |
| 20 | (3-phenoxyphenyl)-CH=/pyrrolidinone N-CH$_2$-CH=CH$_2$ | $C_{20}H_{19}NO_2$ (305.36) | 90~92 | 78.39 | 78.66 | 6.53 | 6.27 | 4.23 | 4.59 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 21 | (3-phenoxyphenyl)-CH-lactam-N-CH=CH$_2$ | C$_{19}$H$_{17}$NO$_2$ (291.33) | 107~111 | 78.04 | 78.33 | 6.12 | 5.88 | 4.47 | 4.81 |
| 22 | (3-phenoxyphenyl)-CH-lactam-N-OMe | C$_{18}$H$_{17}$NO$_3$ (295.32) | Oil | 73.51 | 73.20 | 5.62 | 5.80 | 4.43 | 4.74 |
| 23 | (3-phenoxyphenyl)-CH-lactam-N-(CH$_2$)$_2$OMe | C$_{20}$H$_{21}$NO$_3$ (323.38) | Oil | 74.64 | 74.28 | 6.41 | 6.55 | 4.72 | 4.33 |
| 24 | (3-phenoxyphenyl)-CH-lactam-N-(CH$_2$)$_2$O-tetrahydropyranyl | C$_{24}$H$_{27}$NO$_4$ (393.46) | 58~60 | 73.44 | 73.26 | 6.76 | 6.92 | 3.81 | 3.56 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 25 | 3-phenoxybenzylidene pyrrolidinone N-(CH$_2$)$_2$OH | C$_{19}$H$_{19}$NO$_3$ (309.35) | 74~76 | 73.38 | 73.76 | 5.97 | 6.19 | 4.24 | 4.53 |
| 26 | 3-phenoxybenzylidene pyrrolidinone N-CH$_2$CH$_2$F | C$_{19}$H$_{18}$FNO$_2$ (311.34) | 88~90 | 73.05 | 73.30 | 5.60 | 5.83 | 4.74 | 4.50 |
| 27 | 3-phenoxybenzylidene pyrrolidinone N-(CH$_2$)$_2$Cl | C$_{19}$H$_{18}$ClNO$_2$ (327.77) | 110~113 | 69.98 | 69.62 | 5.36 | 5.53 | 4.64 | 4.27 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 28 | 3-phenoxybenzylidene pyrrolidinone N-CH₂CO₂C₂H₅ | $C_{21}H_{21}NO_4$ (351.39) | 96~97 | 71.70 | 71.78 | 5.99 | 6.02 | 3.77 | 3.99 |
| 29 | 3-phenoxybenzylidene pyrrolidinone N-CH₂CO₂H | $C_{19}H_{17}NO_4$ (323.33) | 137~139 | 70.22 | 70.57 | 5.46 | 5.30 | 4.04 | 4.33 |
| 30 | 3-phenoxybenzylidene pyrrolidinone N-CONH₂ | $C_{18}H_{16}N_2O_3$ (308.32) | 198~199.5 | 70.27 | 70.11 | 5.11 | 5.23 | 9.20 | 9.09 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 31 | (3-phenoxyphenyl)CH=C(C=O)N-O-CONH-(4-methoxyphenyl) pyrrolidinone | C$_{25}$H$_{22}$N$_2$O$_4$ (414.44) | 141~145 | 72.17 | 72.45 | 5.20 | 5.35 | 6.39 | 6.76 |
| 32 | (3-phenoxyphenyl)CH=C(C=O)N-CH$_2$CONH$_2$ pyrrolidinone | C$_{19}$H$_{18}$N$_2$O$_3$ (322.35) | 176~180 | 70.42 | 70.79 | 5.34 | 5.63 | 9.01 | 8.69 |
| 33 | (3-phenoxyphenyl)CH=C(C=O)N-(CH$_2$)$_2$CONH$_2$ pyrrolidinone | C$_{20}$H$_{20}$N$_2$O$_3$ (336.38) | 126~128 | 71.12 | 71.41 | 6.15 | 5.99 | 8.07 | 8.33 |

TABLE 1-continued

| Compound No. | Structure | Molecular formula (Molecular weight) | m.p. (°C) | Elemental analysis | | | | | |
|---|---|---|---|---|---|---|---|---|---|
| | | | | C | | H | | N | |
| | | | | Found | Cal. | Found | Cal. | Found | Cal. |
| 34 | ![structure with CH₂CONHCH₃] | $C_{20}H_{20}N_2O_3$ (336.38) | 156~157.5 | 71.24 | 71.41 | 5.71 | 5.99 | 8.59 | 8.33 |
| 35 | ![structure with CH₂CON(CH₃)₂] | $C_{21}H_{22}N_2O_3$ (350.40) | 126~127 | 72.16 | 71.98 | 6.14 | 6.33 | 8.27 | 8.00 |
| 36 | ![structure with CH₂CON(CH₂)₂N(CH₃)₂ and H] | $C_{23}H_{27}N_3O_3$ (393.47) | 109~110 | 70.41 | 70.20 | 6.78 | 6.92 | 10.92 | 10.68 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 37 | [3-phenoxyphenyl-CH=pyrrolidinone-N-CH₂CN] | $C_{19}H_{16}N_2O_2$ (304.33) | 87~91 | 74.65 | 74.98 | 5.41 | 5.30 | 8.87 | 9.21 |
| 38 | [3-phenoxyphenyl-CH=pyrrolidinone-N-N(CH₃)₂] | $C_{19}H_{20}N_2O_2$ (308.37) | 141~141.5 | 73.87 | 74.00 | 6.62 | 6.54 | 8.94 | 9.09 |
| 39 | [3-phenoxyphenyl-CH=pyrrolidinone-N-(CH₂)₂NH₂·HCl] | $C_{19}H_{21}ClN_2O_2$ (344.84) | 184~186 | 66.43 | 66.18 | 6.31 | 6.17 | 8.39 | 8.12 |

TABLE 1-continued

| Compound No. | Structure | Molecular formula (Molecular weight) | m.p. (°C.) | Elemental analysis ||||||
|---|---|---|---|---|---|---|---|---|---|
| | | | | C || H || N ||
| | | | | Found | Cal. | Found | Cal. | Found | Cal. |
| 40 | (structure: 3-phenoxybenzylidene pyrrolidinone with N-(CH₂)₂N(CH₃)₂) | C₂₁H₂₄N₂O₂ (336.42) | 120~123 | 74.72 | 74.97 | 7.01 | 7.19 | 8.10 | 8.33 |
| 41 | (structure: 3-phenoxybenzylidene pyrrolidinone with N-COCH₃) | C₁₉H₁₇NO₃ (307.33) | 135~137 | 74.41 | 74.25 | 5.72 | 5.58 | 4.29 | 4.56 |
| 42 | (structure: 3-phenoxybenzylidene pyrrolidinone with N-CO-phenyl) | C₂₄H₁₉NO₃ (369.40) | 110~113 | 78.35 | 78.03 | 5.30 | 5.18 | 3.96 | 3.79 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 43 | (structure with OCH₃ substituent) | C₂₅H₂₁NO₄ (399.43) | 143~147 | 74.82 | 75.17 | 5.06 | 5.30 | 3.19 | 3.51 |
| 44 | (structure with COCH=CH-phenyl) | C₂₆H₂₁NO₃ (395.44) | 115~119 | 78.62 | 78.96 | 5.16 | 5.35 | 3.33 | 3.54 |
| 45 | (structure with CH₂COCH₃) | C₂₀H₁₉NO₃ (321.36) | 139~141 | 74.56 | 74.74 | 6.07 | 5.96 | 4.11 | 4.36 |

TABLE 1-continued

| Compound No. | Structure | Molecular formula (Molecular weight) | m.p. (°C.) | Elemental analysis ||||||
|---|---|---|---|---|---|---|---|---|---|
| | | | | C || H || N ||
| | | | | Found | Cal. | Found | Cal. | Found | Cal. |
| 46 | 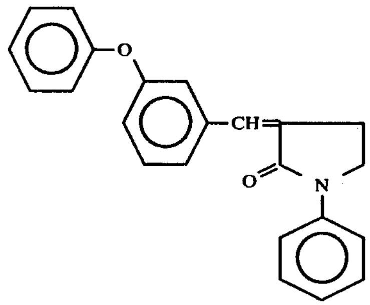 | C₂₃H₁₉NO₂ (341.39) | 160~162 | 81.06 | 80.91 | 5.53 | 5.61 | 4.47 | 4.10 |
| 47 | 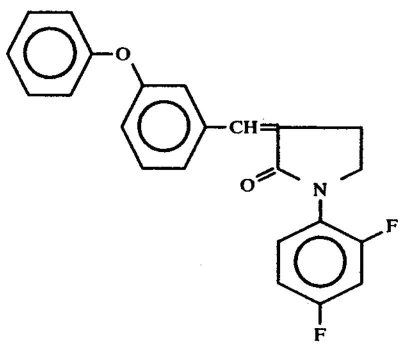 | C₂₃H₁₇F₂NO₂ (377.39) | 108~108.5 | 73.09 | 73.20 | 4.38 | 4.54 | 3.88 | 3.71 |
| 48 | 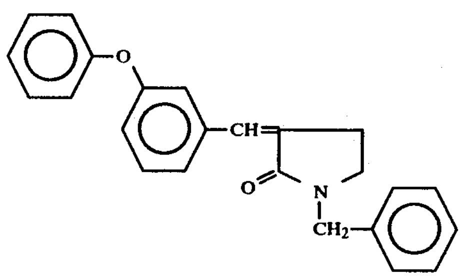 | C₂₄H₂₁NO₂ (355.42) | 122~124 | 80.95 | 81.10 | 6.02 | 5.96 | 4.21 | 3.94 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 49 | (3-phenoxyphenyl)-CH=C, N-CH₂-(4-methoxyphenyl) lactam | C₂₅H₂₃NO₃ (385.44) | 110~112.5 | 78.16 | 77.90 | 5.89 | 6.01 | 3.33 | 3.63 |
| 50 | (3-phenoxyphenyl)-CH=C, N-CH₂-(4-chlorophenyl) lactam | C₂₄H₂₀ClNO₂ (389.88) | 130~131 | 73.76 | 73.94 | 5.25 | 5.17 | 3.21 | 3.59 |
| 51 | (3-phenoxyphenyl)-CH=C, N-CH₂CH₂-phenyl lactam | C₂₅H₂₃NO₂ (369.44) | 98~100 | 81.35 | 81.26 | 6.24 | 6.28 | 3.50 | 3.79 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 52 | 3-phenoxyphenyl-CH=C(CO-NH-CH(CH₃)-) | C₁₈H₁₇NO₂ (279.32) | 105~108 | 77.56 | 77.39 | 6.01 | 6.13 | 4.76 | 5.01 |
| 53 | 3-phenoxyphenyl-CH=C(CO-N(CH₂CH₃)-CH(CH₃)-) | C₂₀H₂₁NO₂ (307.38) | Oil | 78.46 | 78.14 | 6.69 | 6.89 | 4.89 | 4.56 |
| 54 | 3-phenoxyphenyl-CH=C(CO-N(CH₂CH₃)-CH(OH)-) | C₁₉H₁₉NO₃ (309.35) | 104~107 | 74.02 | 73.76 | 6.33 | 6.19 | 4.17 | 4.53 |
| 55 | 3-phenoxyphenyl-CH=C(CO-NH-CH(OCH₃)-) | C₁₈H₁₇NO₃ (295.32) | 137.5~138.5 | 73.41 | 73.20 | 5.67 | 5.80 | 4.50 | 4.74 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 56 | 3-phenoxyphenyl-CH=C(OCH₂CH₃)-C(=O)-NH (lactam with OCH₂CH₃ substituent) | C₁₉H₁₉NO₃ (309.35) | 129~130 | 73.67 | 73.76 | 6.21 | 6.19 | 4.29 | 4.53 |
| 57 | as above with N-CH₂CH₃ | C₂₁H₂₃NO₃ (337.40) | Oil | 74.48 | 74.75 | 6.98 | 6.87 | 3.79 | 4.15 |
| 58 | as above with CH₂OH | C₁₈H₁₇NO₃ (295.32) | Oil | 73.51 | 73.20 | 5.65 | 5.80 | 4.98 | 4.74 |
| 59 | as above with pyrrolidinyl | C₂₁H₂₂N₂O₂ (334.40) | 126~127 | 75.62 | 75.42 | 6.77 | 6.63 | 7.64 | 8.38 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 60 | 3-phenoxyphenyl-CH= lactam with CH₃ branch, NH | C₁₈H₁₇NO₂ (279.32) | Oil | 77.67 | 77.39 | 5.92 | 6.13 | 5.36 | 5.01 |
| 61 | 3-phenoxyphenyl-CH= lactam with CH₃ branch, N-CH₂CH₃ | C₂₀H₂₁NO₂ (307.38) | Oil | 77.91 | 78.14 | 6.80 | 6.89 | 4.74 | 4.56 |
| 62 | 3-phenoxyphenyl-CH= lactam with phenyl branch, NH | C₂₃H₁₉NO₂ (341.39) | 183~188 | 80.57 | 80.91 | 5.97 | 5.61 | 3.76 | 4.10 |
| 63 | 3-phenoxyphenyl-CH= pyrrolidine, NH | C₁₇H₁₇NO (251.31) | Oil | 81.51 | 81.24 | 6.97 | 6.82 | 5.20 | 5.57 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 64 | [3-phenoxyphenyl-CH= with pyrrolidine N·HCl] | $C_{17}H_{18}NOCl$ (287.81) | 127~128.5 | 71.16 | 70.94 | 6.02 | 6.30 | 4.65 | 4.86 |
| 65 | [3-phenoxyphenyl-CH= with piperidine N–CH$_3$] | $C_{18}H_{19}NO$ (265.34) | Oil | 81.72 | 81.47 | 7.29 | 7.22 | 4.96 | 5.28 |
| 66 | [3-phenoxyphenyl-CH= with piperidine N–CH$_2$CH$_3$] | $C_{19}H_{21}NO$ (279.37) | Oil | 81.96 | 81.68 | 7.73 | 7.58 | 4.74 | 5.01 |
| 67 | [3-phenoxyphenyl-CH= with piperidine N·(CO$_2$H)$_2$ CH$_2$CH$_3$] | $C_{21}H_{23}NO_5$ (369.40) | 133~136 | 67.89 | 68.28 | 6.00 | 6.28 | 4.14 | 3.79 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 68 | 3-phenoxyphenyl-CH=pyrrolidine-N-(CH$_2$)$_3$CH$_3$ | C$_{21}$H$_{25}$NO (307.42) | Oil | 82.39 | 82.04 | 8.40 | 8.20 | 4.27 | 4.56 |
| 69 | 3-phenoxyphenyl-CH=pyrrolidine-N-CH$_2$CH=CH$_2$ | C$_{20}$H$_{21}$NO (291.38) | Oil | 82.71 | 82.44 | 7.13 | 7.26 | 5.14 | 4.81 |
| 70 | 3-phenoxyphenyl-CH=pyrrolidine-N-(CH$_2$)$_2$O-tetrahydropyran | C$_{24}$H$_{29}$NO$_3$ (379.48) | Oil | 75.67 | 75.96 | 7.84 | 7.70 | 3.46 | 3.69 |
| 71 | 3-phenoxyphenyl-CH=pyrrolidine-N-(CH$_2$)$_2$OH | C$_{19}$H$_{21}$NO$_2$ (295.37) | Oil | 77.63 | 77.26 | 7.38 | 7.17 | 4.36 | 4.74 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 72 | phenoxyphenyl-CH=–N–CO₂CH₂CH₃ | C₂₀H₂₁NO₃ (323.38) | Oil | 74.67 | 74.28 | 6.81 | 6.55 | 4.65 | 4.33 |
| 73 | phenoxyphenyl-CH=–N–CONH₂ | C₁₈H₁₈N₂O₂ (294.34) | 133~138 | 73.09 | 73.45 | 6.52 | 6.16 | 9.18 | 9.52 |
| 74 | phenoxyphenyl-CH=–N–COCH₃ | C₁₉H₁₉NO₂ (293.35) | Oil | 77.44 | 77.79 | 6.79 | 6.53 | 4.41 | 4.77 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 75 | (3-phenoxyphenyl)-CH=CH-CH(CH₃)-CH₂-N(CH₂CH₃)-CH₂ ring | C₂₀H₂₃NO (293.39) | Oil | 81.52 | 81.87 | 7.77 | 7.90 | 4.42 | 4.77 |
| 76 | (3-phenoxyphenyl)-CH=C(CH₃)-CH-CH₂-N(CH₂CH₃)-CH₂ ring | C₂₀H₂₃NO (293.39) | Oil | 82.16 | 81.87 | 8.01 | 7.90 | 4.50 | 4.77 |
| 77 | (3-phenoxyphenyl)-CH=C(CH₂CH₃)- pyrrolidine NH | C₁₉H₂₁NO (279.37) | Oil | 82.90 | 81.68 | 7.75 | 7.58 | 4.69 | 5.01 |
| 78 | (3-phenoxyphenyl)-CH=C(CH₂CH₃)- piperidine N-CH₂CH₃ | C₂₁H₂₅NO (307.42) | Oil | 82.37 | 82.04 | 8.11 | 8.20 | 4.23 | 4.56 |

TABLE 1-continued

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 79 | ❲structure: 3-phenoxyphenyl-CH=, CH₃(CH₂)₃, N-CH₂CH₃ pyrrolidine❳ | C₂₃H₂₉NO (335.47) | Oil | 82.02 | 82.34 | 8.60 | 8.71 | 4.49 | 4.18 |
| 80 | ❲structure: 3-phenoxyphenyl-CH=, CH₃CH₂, N-COCH₃ pyrrolidine❳ | C₂₁H₂₃NO₂ (321.40) | Oil | 78.12 | 78.47 | 7.29 | 7.21 | 4.07 | 4.36 |
| 81 | ❲structure: 3-phenoxybenzyl pyrrolidinone❳ | C₁₇H₁₇NO₂ (267.31) | 90~93 | 76.74 | 76.38 | 6.15 | 6.41 | 5.51 | 5.24 |

TABLE 1-continued

| Compound No. | Structure | Molecular formula (Molecular weight) | m.p. (°C.) | Elemental analysis ||||||
|---|---|---|---|---|---|---|---|---|---|
| | | | | C ||  H || N ||
| | | | | Found | Cal. | Found | Cal. | Found | Cal. |
| 82 | 3-phenoxybenzyl-N-ethyl pyrrolidinone structure | C₁₉H₂₁NO₂ (295.37) | Oil | 77.59 | 77.26 | 7.50 | 7.17 | 4.98 | 4.74 |
| 83 | 3-phenoxybenzyl-N-ethyl pyrrolidine structure | C₁₉H₂₃NO (281.38) | Oil | 81.36 | 81.10 | 8.08 | 8.24 | 5.32 | 4.98 |
| 84 | 3-phenoxybenzylidene-N-isopropyl pyrrolidine structure | C₂₀H₂₃NO (293.39) | 72~78 | 81.49 | 81.87 | 8.18 | 7.90 | 4.42 | 4.77 |

TABLE 1-continued

| Compound No. | Structure | Molecular formula (Molecular weight) | m.p. (°C.) | Elemental analysis |||||| 
| | | | | C ||  H || N ||
| | | | | Found | Cal. | Found | Cal. | Found | Cal. |
|---|---|---|---|---|---|---|---|---|---|
| 85 | (3-phenoxyphenyl)-CH=, N-cyclopropyl pyrrolidine structure | C$_{20}$H$_{21}$NO (291.38) | Oil | 82.78 | 82.44 | 7.39 | 7.26 | 5.17 | 4.81 |
| 86 | (3-phenoxyphenyl)-CH=, thiolactam (N-H, C=S) structure | C$_{17}$H$_{15}$NOS (281.38) | 141.5~142 | 72.31 | 72.57 | 5.53 | 5.37 | 4.64 | 4.98 |

Cal.: Calculation

Among the phenoxybenzene derivatives (I) of the present invention, salts can be formed with bases in following cases.

That is, in the case that $R^6$ is hydrogen atom in the compound (I) wherein $R^1$ is $OR^6$; in the case that $R^9$ is hydrogen atom in the compound (I) wherein $R^3$ is $-(CH_2)n^1R^7$ and $R^7$ is $-COOR^9$; similarly in the case that $R^7$ is

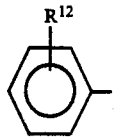

$R^{12}$ is $OR^{13}$ and $R^{13}$ is hydrogen atom; in the case that $R^{20}$ is hydrogen atom in the compound (I) wherein $R^7$ is $-COR^{18}$, $R^{18}$ is

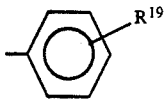

and $R^{19}$ is $-OR^{20}$; in the case that $R^7$ is

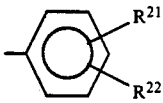

$R^{21}$ and $R^{22}$ are independently $-OR^{23}$ and $OR^{24}$ and $R^{23}$ and/or $R^{24}$ are/is hydrogen atom; in the case that Y is sulfur atom in the compound (I) wherein X is

the phenoxybenzene derivative of the present invention can form a salt with a base.

On the other hand, among the phenoxybenzene derivatives (I) of the present invention, salts can be formed with acids in following cases.

That is, in the case that $R^2$ is amino group; in the case that $R^{10}$ and $R^{11}$ are independently

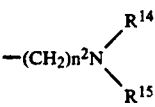

wherein $R^{14}$, $R^{15}$ and $n^2$ are the same as above defined in the compound (I) wherein $R^3$ is $-(CH_2)n^1R^7$ and $R^7$ is

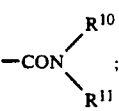

in the case that $R^7$ is

wherein $R^{16}$ and $R^{17}$ are the same as above defined; in the case that $R^{25}$ is pyrrolidyl group in the compound (I) wherein $R^4$ is $-(CH_2)n^3R^{25}$; in the case that Y is sulfur atom in the compound wherein X is

in the case that X is $-CHR^{27}-$ wherein $R^{27}$ is the same as above defined, the phenoxybenzene derivative of the present invention can form a salt with an acid.

As the salts of phenoxybenzene derivative of the present invention, there are, for example, (1) a salt with a metal such as an alkaline metal, an alkaline earth metal or aluminum, (2) an ammonium salt (3) a salt with an organic base such as methylamine, ethylamine, diethylamine, triethylamine, pyrrolidine, piperidine, morphorine, hexamethyleneimine, aniline or pyridine, (4) a salt with an organic acid such as formic acid, acetic acid, trichloroacetic acid, oxalic acid, maleic acid, tartaric acid, methanesulfonic acid, benzenesulfonic acid or toluenesulfonic acid, (5) a salt with an inorganic acid such as chloric acid, hydrobromic acid, sulfuric acid or phosphoric acid, (6) a salt with an amino acid such as arginine, glutamic acid or ornithine.

When the above mentioned salts are used as a cognition enhancer or an antidepressant, pharmacologically acceptable salts are selected.

Physiological tests with the compounds of the present invention are described below.

In order to examine effects of the compounds of the present invention, there were examined an anti-amnesic effect and a binding ability to M1 receptor as a cognition enhancer and an effect on a forced swimming test with rats as an antidepressant.

These effects and acute toxicity were proved by the following tests.

As experimental animals, Wistar male rats and ddY male mice were used for the tests after they were housed for a week under every 12 hours' dark-light cycle at room temperature of 24° to 26° C.

(1) Anti-amnesic effect:

The effect on experimental amnesia in mice induced by cycloheximide was evaluated.

METHOD

The experiment was carried out using an experimental apparatus of passive avoidance task for mice (made by Ohara-ika-sangyo K. K.) comprising a box divided into the two compartments of dark and light. That is, the dark compartment [a box having a reverse trapezoid cross section (height: 8 cm, base line: 5 cm, oblique line: 9.5 cm) and having the length of 14 cm] was shield from a light with a black plastic case and was floored with stainless grids for giving an electrical shock so that an electricity might be turned on a determined time after interception of a photobeam placed in the dark compartment. The light compartment made of transparent plastic (a box of the same shape as that of the dark compartment having the length of 16 cm, lightened from a location spaced 25 cm above by a 60 W electric lamp) was provided adjacent to the dark compartment. Between the two compartments, there was provided a circular entrance having the diameter of 3 cm with a guillotine door which could be opened and closed. By using the above-mentioned dark-light box, the experiment was carried out according to the following procedure.

A mouse (5 week-old) previously conditioned in the dark-light box was put in the light compartment and the guillotine door was opened. Three seconds after the mouse moved into the dark compartment and interrupted the photobeam, 0.3 mA electrical shock was given to limbs for 3 seconds from the floor grid (aquisition trial). Just after the mouse rushed into the light compartment, the door was shut and the rat in the light compartment was picked out to return to his home cage. After 24 hours, the mouse was placed again in the light compartment and the period from the opening of the guillotine door to the time the mouse completely entered the dark compartment was recorded maximally 300 seconds as a step-through latency (retention trial).

The amnesia was induced by subcutaneous injection of cycloheximide (120 mg/kg) dissolved in saline 10 minutes before the aquisition trial. As a control, the same amount of saline alone was administered. Every test compound was suspended in a distilled water containing 2.5% of gum arabic and 0.2% of Tween 80, and orally administered at a dose of 3 mg/kg or 1 mg/kg 1 hour before the aquisition trilal.

A ratio of number of mice showing the step-through latency of more than 100 seconds in the group was defined as a ratio of memory for convenience's sake.

RESULTS

The effects on the amnesia induced by cycloheximide are shown in Table 2.

The step-through latency in Table 2 was the mean value for each treated group.

From the results, it is recognized that the compound of the present invention having the formula (I) has a potent anti-amnesic effect. The compound No. corresponds to the compound No. in Table 1.

TABLE 2

| Compound No. | Dose (mg/kg) | Cyclo-heximide | Number of animals used | Step-through latency (sec.) | Ratio of memory (%) |
| --- | --- | --- | --- | --- | --- |
| Control | — | — | 13 | 217 | 77 |
|  |  | + | 18 | 30 | 6 |
| Indeloxazine hydrochloride | 3 | + | 7 | 131 | 43 |
| 1 | 3 | + | 18 | 198 | 72 |
| 2 | 3 | + | 8 | 188 | 75 |
| 3 | 3 | + | 8 | 173 | 75 |
| 5 | 3 | + | 8 | 134 | 50 |
| 6 | 3 | + | 13 | 101 | 31 |
| 7 | 3 | + | 8 | 113 | 50 |
| 8 | 3 | + | 8 | 118 | 38 |
| 9 | 3 | + | 8 | 151 | 75 |
| 10 | 3 | + | 10 | 127 | 80 |
| 11 | 3 | + | 8 | 182 | 63 |
| 12 | 3 | + | 8 | 152 | 63 |
| 13 | 3 | + | 8 | 132 | 38 |
| 14 | 3 | + | 4 | 100 | 25 |
| 16 | 3 | + | 8 | 176 | 75 |
| 19 | 1 | + | 4 | 177 | 75 |
| 22 | 3 | + | 8 | 100 | 50 |
| 23 | 3 | + | 8 | 71 | 50 |
| 24 | 3 | + | 8 | 109 | 38 |
| 26 | 1 | + | 4 | 196 | 75 |
| 28 | 3 | + | 8 | 100 | 50 |
| 31 | 3 | + | 4 | 100 | 50 |
| 32 | 1 | + | 4 | 94 | 50 |
| 35 | 1 | + | 4 | 103 | 50 |
| 36 | 1 | + | 4 | 163 | 75 |
| 37 | 1 | + | 4 | 110 | 50 |
| 38 | 1 | + | 4 | 100 | 50 |
| 40 | 1 | + | 4 | 116 | 50 |
| 41 | 3 | + | 8 | 80 | 25 |
| 42 | 1 | + | 4 | 80 | 25 |
| 43 | 3 | + | 8 | 179 | 100 |
| 44 | 3 | + | 8 | 132 | 38 |
| 45 | 1 | + | 4 | 169 | 50 |
| 46 | 3 | + | 8 | 172 | 75 |
| 48 | 3 | + | 8 | 117 | 63 |
| 49 | 1 | + | 4 | 102 | 50 |
| 50 | 3 | + | 4 | 100 | 50 |
| 52 | 3 | + | 4 | 120 | 50 |
| 53 | 3 | + | 8 | 114 | 50 |
| 55 | 3 | + | 4 | 80 | 25 |
| 56 | 3 | + | 8 | 129 | 63 |
| 57 | 3 | + | 4 | 157 | 50 |
| 58 | 1 | + | 4 | 111 | 50 |
| 59 | 3 | + | 8 | 157 | 50 |
| 61 | 1 | + | 4 | 90 | 50 |
| 62 | 3 | + | 4 | 170 | 50 |
| 64 | 3 | + | 8 | 150 | 63 |
| 65 | 1 | + | 4 | 117 | 50 |
| 66 | 0.3 | + | 8 | 221 | 75 |
| 67 | 1 | + | 4 | 100 | 50 |
| 68 | 1 | + | 4 | 179 | 75 |
| 69 | 1 | + | 4 | 102 | 50 |
| 71 | 1 | + | 4 | 212 | 75 |
| 73 | 1 | + | 4 | 119 | 50 |
| 74 | 1 | + | 4 | 107 | 50 |
| 75 | 1 | + | 4 | 160 | 50 |
| 76 | 1 | + | 4 | 109 | 50 |
| 78 | 1 | + | 4 | 132 | 75 |
| 79 | 1 | + | 4 | 168 | 50 |
| 80 | 1 | + | 4 | 100 | 50 |
| 81 | 1 | + | 4 | 70 | 25 |
| 82 | 3 | + | 8 | 102 | 38 |
| 83 | 1 | + | 4 | 188 | 100 |
| 84 | 1 | + | 4 | 176 | 75 |
| 85 | 1 | + | 4 | 97 | 25 |
| 86 | 3 | + | 4 | 70 | 25 |

(2) Receptor binding activity

The binding ability of the test compounds to M1 was determined according to a modification of the method of Watson et al. (Life Sci., 32, 3001 (1983)). Concretely, rat's brain except for cerebellum was homogenized and added with 1 μM of a test compound and 1 nM of [3H]pyrenzepine, M1 specific antagonist. The mixture was incubated for 1 hour. The inhibition rate (%) of the binding with [3H]pyrenzepine was evaluated. The results are shown in Table 3. The higher inhibition means the higher affinity of the test compound for M1 receptor.

TABLE 3

| Compound No. | Conc. (μM) | Inhibition |
| --- | --- | --- |
| 10 | 10 | 90 |
| 11 | 10 | 58 |
| 16 | 10 | 75 |
| 20 | 10 | 88 |
| 22 | 10 | 63 |
| 26 | 10 | 87 |
| 32 | 10 | 91 |
| 59 | 10 | 56 |
| 64 | 10 | 90 |
| 65 | 10 | 52 |
| 66 | 1 | 82 |
| 67 | 1 | 78 |
| 75 | 1 | 65 |

TABLE 3-continued

| Compound No. | Conc. (μM) | Inhibition |
|---|---|---|
| 76 | 1 | 80 |
| 84 | 1 | 75 |

The binding ability to M2 was determined according to a modification of the method of Buckley et al. (Mol. Pharmacol. 35, 469 (1989)). Concretely, an inhibition of binding was examined by adding 10 μM of the test compound and 0.2 nM of [3H]N-methylscopolamine to a membrane fraction of cardiac muscle of a rat. As a result, each inhibition was not more than 50% and therefore the binding ability of the compound of the present invention to M2 is recognized to be low.

Muscarinic cholinergic receptors are now classified into three kinds of subtypes (M1, M2 and M3). Mainly, M1 is distributed in central nerve, M2 in heart and M3 in ganglion. Therefore drugs which stimulate M2 or M3 are likely to cause peripheral side effects such as cardiac depression or tremor. So selectivity toward M1 is preferable for the aim of potentiating central cholinergic neuron.

That is, a selective muscarinic M1 agonist is considered to have an ability improving a disturbance of memory or perception in senile dementia.

As described above it has been proved that the compound of the present invention has the selective affinity for M1 receptor and therefore usable for the treatment of diseases due to an alteration of central nervous system, particularly diseases caused by a lowering of cholinergic function, such as Alzheimer's disease, senile dementia of Alzheimer's type, Huntington's chorea, Pick disease and tardive dyskinesia.

(3) Antidepressant activity

The effect was examined in a forced swimming test using rats.

METHODS

The experiment was carried out according to a modification of the method of Porsort et al. (Eur. J. Pharmacol., 47, P 379 (1978)). That is, a rat (5 week-old) was placed into a glass cylinder having the inside diameter of 18 cm and the height of 40 cm which contained water (water temperature: 25° C.) up to its height of 15 cm. After 15 minutes, the rat was picked up followed by drying and then returned to his home cage. After 24 hours, the rat was again placed into the water in the same cylinder. The duration of immobility (the time rat kept motionless) was accumulatively measured with a stopwatch for five minutes (a five minutes' test). Each test compound was suspended in saline. The administration was carried out three times, at 24, 5 and 1 hour before the five minutes' test in case of an intraperitoneal administration or with only a single administration at 1 hour before the five minutes' test in case of an oral administration to examine the antidepressant effect.

RESULTS

The results are shown in Table 4.

The duration of immobility in Table 4 is the mean value for mice in each group. Suppression is expressed as a ratio in percentage of a reduction of the duration of immobility in the group administered with the test compound to that in the control group administered with saline alone. The higher suppression, namely a large shortening of the duration, means the more potent antidepressant effect.

As shown in Table 2, the compound of the present invention showed a remarkable reduction of the duration of immobility by oral administration. On the other hand, the oral administration of a tricyclic antidepressant, imipramine which is a positive control showed no effect.

Although the similar experiment was carried out in an oral administration with respect to pargyline which is a representative monoamine oxidase inhibitor, its administration caused prolongation of the duration of immobility.

TABLE 4

| | Test compound | Dose (mg/kg/time) | Amount of animals used | Duration of immobility (sec.) | Suppresion (%) |
|---|---|---|---|---|---|
| i.p. administration | Saline alone | | 18 | 204 | 0 |
| | Imipramine | 100 | 7 | 79 | 61 |
| | Compound 1 | 1 | 4 | 164 | 20 |
| | | 3 | 4 | 101 | 50 |
| | | 10 | 4 | 71 | 65 |
| | | 30 | 4 | 54 | 74 |
| p.o. administration | Saline alone | | 18 | 205 | 0 |
| | Imipramine | 30 | 4 | 210 | −2 |
| | Pargyline | 30 | 3 | 244 | −19 |
| | Compound 1 | 0.3 | 6 | 190 | 7 |
| | | 1 | 5 | 165 | 20 |
| | | 3 | 4 | 137 | 33 |
| | | 10 | 4 | 76 | 63 |
| | | 30 | 4 | 34 | 83 |
| | Compound 64 | 30 | 3 | 40 | 82 |

(4) Acute toxicity test

With respect to the compounds 1 to 86 shown in Table 1 as test compounds, the acute toxicity was examined using ddY mice according to the following method.

In each group, six male ddY mice weighing 27 to 30 g were employed. The compounds 1 to 86 suspended in an aqueous solution of 0.5% sodium carboxymethylcellulose were administered orally in a volume of 0.1 ml/10 g body weight. The general symptoms were observed for 2 weeks after the administration. The $LD_{50}$ (mg/kg) values were estimated from the ratio of the number of dead mice to the number of mice used.

As a result, there were observed no dead mice at a dose of 500 mg/kg with respect to the compounds 1 to 62 and 65 to 86 of the present invention. The $LD_{50}$ values of the compounds 1 to 62 and 65 to 86 were estimated to be not less than 500 mg/kg. With respect to the compounds 63 and 64, there were observed no dead mice at a dose of 200 mg/kg. The the $LD_{50}$ of the compounds 63 and 64 were estimated to be not less than 200 mg/kg.

These results proved a low toxicity of the compounds of the present invention.

The cognition enhancers or antidepressants of the present invention can be administered orally, rectally or parentarally in pharmaceutical dosage form, for example, tablets, capsules, fine subtilaes, syrups, suppositories, ointments, injections, and the like.

As for excipients in the formulation of the cognition enhancers or antidepressants of the present invention, organic or inorganic pharmaceutical excipient material is employed in a solid or liquid state, which is usually inactive and suited for oral, rectal or parenteral administration. Examples of such excipient are, for instance, crystalline cellulose, gelatin, lactose, starch, magnesium stearate, talc, vegetable or animal fat and oil, gum polyalkyleneglycol, and the like. The ratio of the compound of the present invention in the formulation may vary in the range from 0.2 to 100%. The cognition enhancers or antidepressants of the present invention may contain other cognition enhancers, antidepressants or any other drugs, which are compatible with the agents of the present invention. In this case, the cognition enhancers or antidepressants of the present invention may not be the principal ingredients in the formulation.

The cognition enhancers or antidepressants of the present invention are administered at a dose where the desired activity is generally achieved without any side effects.

Though a practical dose should be determined by a physician, the compounds of the present invention, as an active ingredient, is generally administered at a dose from 0.01 mg to 10 g, preferably from about 0.1 mg to 5 g, for an adult a day.

The cognition enhancers or antidepressants of the present invention can be administered as a pharmaceutical formulation which contains a unit dose of 0.001 mg to 5 g, preferably 0.1 mg to 1 g of the compounds as an active ingredient.

The present invention is more specifically described and explained by means of the following Examples. The present invention is not limited to Examples.

EXAMPLE 1

Synthesis of the compound 1

Into 2.2 g of sodium hydride (60% dispersion in oil) was added 30 ml of dry tetrahydrofuran (THF) to give a suspension. Separately there was prepared a solution of 6.0 g of m-phenoxybenzaldehyde and 3.8 g of 1-acetyl-2-pyrrolidone which were dissolved in 30 ml of dry THF. The above mentioned solution was added with stirring to the above mentioned suspension on an ice bath. After the addition, the temperature of the mixture was gradually raised to room temperature and the reaction was carried out for 16 hours. After the reaction, the reaction solution was cooled and thereto was added 5 ml of methanol. The resultant mixture was poured into 150 ml of cold water. The mixture was adjusted to pH 2 with 6N sulfuric acid and then extracted four times with 50 ml of chloroform. The extract was dried over anhydrous magnesium sulfate and then the solvent was distilled away under reduced pressure. To the residue was added chloroform to carry out crystallization. Thus 3.0 g (yield: 37%) of the desired compound 1 was obtained. IR spectrum: $\nu_{max}^{KBr}$ cm$^{-1}$: 3178, 3060, 1705, 1657, 1589, 1490, 1243.

$^1$H NMR spectrum ($\delta$, CDCl$_3$-DMSO-d$_6$): 3.06 (2H, dt, J=3 Hz, 6 Hz), 3.50 (2H, t, J=6 Hz), 6.86–7.57 (10H,m), 8.03 (1H, brs).

EXAMPLE 2

Synthesis of the compound 2

The procedure of Example 1 was repeated except for using p-phenoxybenzaldehyde instead of m-phenoxybenzaldehyde in Example 1 to give 1.9 g (yield: 24%) of the desired compound 2.

IR spectrum: $\nu_{max}^{KBr}$ cm$^{-1}$; 3190, 3072, 1687, 1645, 1539, 1491, 1250

$^1$H NMR spectrum ($\delta$, CDCl$_3$-DMSO-d$_6$): 3.06 (2H, dt, J=3 Hz, 6 Hz), 3.43 (2H, t, J=6 Hz), 6.93–7.60 (10H,m), 7.97 (1H, brs).

EXAMPLE 3

Synthesis of the compound 3

The procedure of Example 1 was repeated except for using o-phenoxybenzaldehyde instead of m-phenoxybenzaldehyde in Example 1 to give 1.4 g (yield: 18%) of the desired compound 3.

$^1$H NMR spectrum ($\delta$, CDCl$_3$-DMSO-d$_6$): 3.06 (2H, dt, J=3 Hz, 6 Hz), 3.30 (2H, t, J=6 Hz), 6.76–7.70 (10H, m), 8.05 (1H, brs).

EXAMPLE 4

Synthesis of the compound 4

The procedure of Example 1 was repeated except for using 3-(4-methylphenoxy)benzaldehyde instead of m-phenoxybenzaldehyde in Example 1 to give 2.8 g (yield: 33%) of the desired compound 4.

$^1$H NMR spectrum ($\delta$, CDCl$_3$-DMSO-d$_6$): 2.33 (3H, s) 3.05 (2H, dt, J=3 Hz, 6 Hz), 3.43 (2H, t, J=6 Hz), 6.80–7.47 (9H, m), 8.00 (1H, brs).

EXAMPLE 5

Synthesis of the compound 7

The procedure of Example 1 was repeated except for using 3-nitro-4-phenoxybenzaldehyde instead of m-phenoxybenzaldehyde in Example 1 to give 3.30 g (yield: 36%) of the desired compound 7.

$^1$H NMR spectrum ($\delta$, CDCl$_3$): 3.16 (2H, dt, J=3 Hz, 6 Hz), 3.60 (2H, t, J=6 Hz), 6.93–7.67 (9H,m), 8.06 (1H, d, J=2 Hz).

EXAMPLE 6

Synthesis of the compound 8

Into 20 ml of concentrated hydrochloric acid and 10 ml of ethanol was added 2 g of the compound 7. To the mixture was added 8.8 g of tin (II) chloride dihydrate dissolved in 15 ml of ethanol. The mixture was stirred at room temperature over night and slightly concentrated. The resultant precipitate was filtrated. The residue was recrystallized from a mixed solvent of ethanol and concentrated hydrochloric acid to give 0.9 g (yield: 44.1%) of the desired compound 8.

$^1$H NMR spectrum ($\delta$, DMSO-d$_6$): 3.06 (2H, brt), 3.40 (2H, t, J=6 Hz), 6.80–7.73 (12H, m), 8.13 (1H, brs).

EXAMPLE 7

Synthesis of the compound 10

To 0.54 g (13.2 mmole) of sodium hydride (oiliness, content: 60%) was added DMF. Thereto was added 3.5 g (13.2 mmole) of the compound 1 to give a suspension. To the cooled above mentioned suspension was added a solution containing 1.1 ml (13.2 mmole) of ethyl iodide in DMF with stirring. Then the reaction was carried out at room temperature over night. After the reaction, water was added to the reaction solution with cooling. Then the mixture was acidified with diluted hydrochloric acid and extracted with chloroform. The extract solution was washed with water and the solvent was distilled away under reduced pressure. The crude product was purified by silica gel column chromatography (eluting solvent: ethyl acetate/n-hexane=½) to give 1.4 (yield: 36%) of the desired compound 10.

$^1$H NMR spectrum ($\delta$, CDCl$_3$): 1.17 (3H, t, J=7.5 Hz), 2.95 (2H, dt, J=3 Hz, 6 Hz), 3.41 (2H, t, J=4.5 Hz), 3.51 (2H, q, J=7.5 Hz), 6.90–7.45 (10H, m)

EXAMPLE 8

Synthesis of the compound 12

The procedure of the Example 7 was repeated except for using n-butyl bromide instead of ethyl iodide in Example 7. The crude product was purified by silica gel column chromatography (eluting solvent: chloroform) to give 0.13 g (yield: 7%) of the desired compound 12.

$^1$H NMR spectrum ($\delta$, CDCl$_3$): 0.95 (3H, t, J=6 Hz), 1.15–1.65 (4H,m) 2.95 (2H, dt, J=3 Hz, 6 Hz), 3.35–3.55 (4H), 6.90–7.44 (10H, m).

EXAMPLE 9

Synthesis of the compound 15

The procedure of Example 1 was repeated except for using m-(p-methylphenoxy)benzaldehyde instead of m-phenoxybenzaldehyde in Example 1 to give 3-[m-(p-methylphenoxy)benzylidene]-pyrrolidin-2-one. A solution containing 2.6 g of the resultant product in dimethylformamide was cooled in an atmosphere of argon and added dropwide to a suspension containing 0.37 g of sodium hydride in dimethylformamide. Thereto was added dropwise 0.75 ml of ethyl iodide. After the addition, the reaction was carried out at room temperature for 18 hours. The reaction solution was cooled and thereto was poured water followed by the neutralization with diluted hydrochloric acid. The solution was extracted with chloroform. The extract was washed with water, dried over magnesium sulfate and then concentrated. The crystallization was carried out from ethyl acetate to give 1.1 g (38%) of the desired compound 15.

$^1$H NMR spectrum ($\delta$, CDCl$_3$): 1.2 (3H, t, J=6 Hz), 2.3 (3H, s), 3.0 (2H, dt, J=3 Hz, 6 Hz), 3.5 (4H, t, J=6 Hz, t, J=6 Hz), 6.9–7.3 (9H, m).

EXAMPLE 10

Synthesis of the compound 17

On an ice bath, to a solution containing 5.0 ml of cyclopropylamine in chloroform was added dropwise a solution containing 16.8 g of 2,4-dibromobutyryl chloride in chloroform. Then thereto was added dropwise 8.88 ml of triethylamine. After the addition the reaction was carried out at room temperature for 18 hours. To the reaction solution was added water. The organic layer thereof was washed with 0.5N hydrochloric acid, saturated aqueous solution of sodium bicarbonate and saturated aqueous solution of sodium chloride successively. The solution was dried over magnesium sulfate and then concentrated to give 16.3 g of N-cyclopropyl-2,4-dibromobutyrylamide.

In anhydrous benzene was dissolved 16.3 g of the resultant amide. Thereto was added 2.53 g of soium hydride (oiliness, content 60%) with cooling. After the addition, the mixture was refluxed for 18 hours. The reaction solution was poured into ice water. The organic layer thereof was dried over magnesium sulfate and then concentrated to give 2.4 g N-cyclopropyl-3-bromopyrrolidin-2-one.

In 3 ml of anhydrous tetrahydrofuran were dissolved 2.4 g of the resultant product and 3.4 g of triphenylphosphine. The solution was reacted at 60° C. for 30 hours. After cooling to room temperature, the solution was filtrated and the solvent was distilled away under reduced pressure. The residue was dissolved in anhydrous ethanol. Thereto were added 1.15 ml of triethylamine and 1.43 ml of m-phenoxybenzaldehyde. The reaction was carried out at 60° C. for 2 hours. After the solvent was distilled away under reduced pressure, the residue was dissolved in chloroform and washed with water. The solution was dried over magnesium sulfate and the concentrated. The concentrate was crystallized from ethyl acetate to give 1.50 g (yield: 42%) of the desired compound 17.

$^1$H NMR spectrum ($\delta$, CDCl$_3$): 0.85 (4H, m), 2.8 (1H, m), 2.9 (2H, dt, J=3 Hz, 6 Hz), 3.4 (2H, t, J=6 Hz), 6.8–7.5 (10H, m).

EXAMPLE 11

Synthesis of the compound 18

In 60 ml of anhydrous ether was dissolved 1.80 g of the compound 2. After cooling, thereto was added 1.0 g of lithium aluminum hydride. After the addition, the mixture was refluxed for 8 hours. After cooling, the reaction solution was diluted with ether and thereto was added methanol. The solution was stirred for a while and then filtrated. The filtrate was concentrated and the residue was dissolved in ether. The solution was washed with water and then concentrated to give 1.21 g (yield: 71%) of the desired compound 18.

$^1$H NMR spectrum ($\delta$, CDCl$_3$): 1.15 (3H, t, J=6 Hz), 2.55 (2H, q, J=6 Hz), 2.75 (4H, s), 3.33 (2H, s), 6.3 (1H, s), 6.9–7.4 (9H, m).

EXAMPLE 12

Synthesis of the compound 19

In 100 ml of dry ether was dissolved 1.0 g of the compound 15 in an atmosphere of nitrogen. The solution was cooled on an ice bath. To the resultant cooled solution was gradually added 0.6 g of lithium aluminum hydride. After the addition, the obtained suspension was heated under reflux with stirring on an oil bath for 8 hours. After the reaction, the reaction solution was cooled. Thereto was added 50 ml of cold water gradually and the mixture was extracted three times with 100 ml of ether. The extract was filtrated and the filtrate was extracted with 50 ml of 2N hydrochloric acid. The extract was cooled on an ice bath and neutralized with potassium carbonate. Then the resultant solution was extracted four times with 100 ml of ether. The solvent was concentrated under reduced pressure. The obtained oily product was subjected to column chromatography with silica gel as a carrier and eluted with chloroform to give 4.4 g (yield: 66%) of the desired compound 19.

$^1$H NMR spectrum ($\delta$, CDCl$_3$): 1.15 (t, J=7 Hz, 3H), 2.33 (s, 3H), 2.53 (q, J=7 Hz, 2H), 2.71 (br, 4H), 3.31 (s, 2H), 6.29 (br, 1H), 6.78–7.27 (m, 9H).

EXAMPLE 13

Synthesis of the compound 21

In 3 ml of benzene was dissolved 0.56 g of the compound 27. Thereto was added 0.11 g of potassium hydroxide and the mixture was refluxed for 22 hours. The solution was cooled to room temperature and concentrated. The concentrated was crystallized from ethy acetate to give 80 mg (yield: 16%) of the desired compound 21.

IR spectrum: $\nu_{max}^{KBr}$cm$^{-1}$: 3400, 1690, 1650, 1630, 1590, 1570, 1490, 1250.

$^1$H NMR spectrum ($\delta$, CDCl$_3$): 3.07 (2H, dt, J=3 Hz, 6 Hz), 3.61 (2H, t, J=6 Hz), 4.52 (2H, m), 6.97–7.41 (11H, m).

EXAMPLE 14

Synthesis of the compound 22

In anhydrous ethanol was dissolved 2 g (4.4 mmole) of (N-methoxy-2-oxopyrrolid-3-yl)-triphenylphosphonium bromide (prepared in the same way as described in J.M.C, 30, 1995 (1987)). Thereto were added 0.69 g (3.5 mmole) of m-phenoxybenzaldehyde and 0.61 ml (4.4 mmole) of triethylamine. The reaction was carried out at 60° C. for 2 hours. After the reaction, the solvent was distilled away under reduced pressure and the residue was dissolved in chloroform. The solution was washed with water and dried over magnesium sulfate. Then the solvent was distilled away under reduced pressure. The residue was purified by silica gel column chromatography (eluting solvent: chloroform) to give 0.12 g (yield 7%) of the desired compound 22.

$^1$H NMR spectrum ($\delta$, CDCl$_3$): 2.97 (2H, dt, J=3 Hz, 6 Hz), 3.60 (2H, t, J=6 Hz), 3.84 (3H, S), 6.88-7.40 (10H, m).

EXAMPLE 15

Synthesis of the compound 23

In an atmosphere of argon dimethylformamide was added to 0.3 g of sodium hydride (oiliness, content: 60%) with cooling to give a suspension. Thereto was added dropwise a solution containing 0.71 ml of 2-bromoethyl methyl ether in dimethylformamide. After the addition, the reaction was carried out at room temperature for 18 hours. After cooling, water was poured into the reaction solution. The solution was acidified with diluted hydrochloric acid and extracted with chloroform. The extract was washed with water and then concentrated to give 0.21 g (9%) of the desired compound 23.

$^1$H NMR spectrum ($\delta$, CDCl$_3$): 2.95 (2H, dt, J=3 Hz, 6 Hz), 3.35 (3H, s), 3.6 (6H, m), 6.85-7.40 (10H, m).

EXAMPLE 16

Synthesis of the compound 24

The procedure of Example 7 was repeated except for using tetrahydropyranyloxyethyl bromide instead of ethyl iodide in Example 7. The crude product was purified by silica gel column chromatography (eluting solvent: ethyl acetate/n-hexane=⅓) to give 1.1 g (yield: 9%) of the desired compound 24.

$^1$H NMR spectrum ($\delta$, CDCl$_3$): 1.60 (6H, m), 3.00 (2H, dt, J=3 Hz, 6 Hz), 3.45-4.05 (9H, m), 4.60 (1H, s), 6.90-7.45 (10H, m).

EXAMPLE 17

Synthesis of the compound 25

In methanol was dissolved 0.8 g (2.0 mmole) of the compound 24. Thereto was added concentrated hydrochloric acid in an amount as a catalyst. The mixture was stirred for 1 hour. After the reaction the solvent was distilled away under reduced pressure. The residue was purified by silica gel column chromatography (eluting solvent: chloroform) to give 0.38 g (yield: 61%) of the desired compound 25.

$^1$H NMR spectrum ($\delta$, CDCl$_3$): 2.88 (2H, dt, J=3 Hz, 6 Hz), 3.18 (1H, brs), 3.40-3.55 (4H), 3.73 (2H, t, J=4.5 Hz), 6.80-7.33 (10H, m).

EXAMPLE 18

Synthesis of the compound 27

Into 0.12 ml of thionyl chloride on an ice bath was added dropwise a solution containing 0.47 g of the compound 25 in chloroform. After the addition, the reaction was carried out at room temperature for 18 hours. The reaction solution was poured into anhydrous ethanol. The mixture was refluxed for a while and then filtrated at a high temperature followed by cooling. Thus 0.11 g (yield: 22%) of the desired compound 27 was obtained.

$^1$H NMR spectrum ($\delta$, CDCl$_3$): 3.0 (2H, dt, J=3 Hz, 6 Hz), 3.6 (2H, t, J=6 Hz), 3.75 (4H, s), 6.88-7.50 (10H, m).

EXAMPLE 19

Synthesis of the compound 28

The procedure of Example 7 was repeated except for using an ester of ethyl bromoacetate instead of ethyl iodide in Example 7. The crude product was purified by silica gel column chromatography (eluting solvent: chloroform) to give 1.7 g (yield: 37%) of the desired compound 28.

$^1$H NMR spectrum ($\delta$, CDCl$_3$): 1.27 (3H, t, J=7.5 Hz),
3.03 (2H, dt, J=3 Hz), 3.60 (2H, t, J=7.5 Hz), 4.10-4.30 (4H), 6.97-7.50 (10H, m).

EXAMPLE 20

Synthesis of the compound 29

In ethanol was dissolved 1.7 g (4.8 mmole) of the compound 28. Thereto was added 2 ml of 10% NaOH aqueous solution and the mixture was stirred for 2 hours. After the reaction, the mixture was acidified with 2N hydrochloric acid and extracted with chloroform. The extract was washed with water and then dried over magnesium sulfate. The solvent was distilled away under reduced pressure. The crude product was purified by silica gel column chromatography (eluting solvent: chloroform) to give 0.77 g (yield: 50%) of the desired compound 29.

$^1$H NMR spectrum ($\delta$, CDCl$_3$): 3.02 (2H, dt, J=3 Hz, 6 Hz), 3.54 (2H, t, J=6 Hz), 4.28 (2H, s), 6.94-7.42 (10H, m).

EXAMPLE 21

Synthesis of the compound 30

In 5 ml of benzene was dissolved 0.4 g of the compound 1. Thereto was added dropwise 0.16 ml of chlorosulfonylisocyanate. The mixture was refluxed for 15 minutes. After cooling to room temperature, 1.7 ml of water was added thereto and the mixture was stirred for 1.5 hours. The mixture was extracted with chloroform. The extract was dried over magnesium sulfate and then concentrated. The concentrate was crystallized from acetonitrile to give 0.3 g (yeild: 65%) of the desired compound 30.

$^1$H NMR spectrum ($\delta$, CDCl$_3$): 3.0 (2H, dt, J=3 Hz, 6 Hz), 3.9 (2H, t, J=6 Hz), 7.0-7.5 (10H, m), 8.4 (2H, br).

EXAMPLE 22

Synthesis of the compound 31

In 50 ml of anhydrous benzene, 1.3 g of the compound 1 and 0.65 ml of 4-methoxyphenylisocyanate were refluxed for 24 hours. The solvent was distilled away under reduced pressure. The residue was dissolved in 25 ml of methylene chloride and the solution was filtrated. The filtrate was concentrated and the concentrate was crystallized from methylene chloride and n-hexane to give 0.9 g (yield: 45%) of the desired compound 31.

$^1$H NMR spectrum ($\delta$, CDCl$_3$): 3.0 (2H, dt, J=3 Hz, 6 Hz), 3.8 (3H, s), 4.0 (2H, t, J=6 Hz), 6.8–7.6 (14H, m).

EXAMPLE 23

Synthesis of the compound 32

In methylene chloride was dissolved 1.0 g (3.1 mmole) of the compound 29. Thereto was added 0.54 ml (6.2 mmole) of thionyl chloride. The mixture was refluxed for 1 hour. The solvent and excess thionyl chloride was distilled away under reduced pressure. The residue was added to a solution containing 2.0 ml (9.3 mmole) of hexamethydisilazane in methylene chloride. The reaction was carried out at room temperature over night. After the reaction, 2 ml of methanol was added to the reaction solution. The mixture was washed with 5% sulfuric acid and then with a saturated aqueous solution of ammonium sulfate. The mixture was dried over magnesium sulfate and the solvent was distilled away under reduced pressure. The crude product was purified by silica gel column chromatography (eluting solvent: chloroform) to give 0.10 g (yield: 10%) of the desired compound 32.

$^1$H NMR spectrum ($\delta$, CDCl$_3$): 3.02 (2H, dt, J=3 Hz, 6 Hz), 3.60 (2H, t, J=7.5 Hz), 4.08 (2H, s), 5.47 (1H, brs), 6.90–7.45 (10H, m).

EXAMPLE 24

Synthesis of the compound 33

The procedure of Example 19 was repeated except for using ethyl bromopropionate instead of ethyl bromoacetate in Example 19 to give N-(2-ethylcarboxy)-3-(m-phenoxybenzylidene)-pyrrolidin-2-one. In a mixed solvent of 24 ml of methylene chloride and 6 ml of dimethylformamide was dissolved 2.3 g of the resultant compound. Thereto were added 0.88 g of 1-hydroxybenzotriazole and 1.28 g of 1,3-dicyclohexylcarbodiimide. The reaction was carried out at room temperature for 30 minutes. Then thereto was added 0.6 ml of 29% aqueous ammonia and the reaction was carried out at room temperature for 3 hours. The reaction solution was filtrated and the filtrate was diluted with 60 ml of methylene chloride. The solution was washed three times with 20 ml of 5% sodium bicarbonate, with water, two times with 20 ml of 5% citric acid and with water successively. The solution was dried over magnesium sulfate and then concentrated. The concentrate was crystallized from methanol to give 0.83 g (yield: 41%) of the desired compound 33.

$^1$H NMR spectrum ($\delta$, CDCl$_3$): 2.61 (2H, t, J=6 Hz), 3.00 (2H, dt, J=3 Hz, 6 Hz), 3.56 (2H, t, J=6 Hz), 3.72 (2H, t, J=6 Hz), 5.4 (1H, br), 6.6 (1H, br), 6.9–7.4 (10H, m).

EXAMPLE 25

Synthesis of the compound 34

In methylene chloride were dissolved 1.1 g of the compound 29 and 0.23 g of dimethylamine hydrochloride followed by cooling. Thereto were added 0.47 ml of triethylamine and 0.78 g of 1-ethyl-3-(3-dimethylaminopropyl)-carbodiimide hydrochloride (w.s.c). After the addition, the reaction was carried out at room temperature for 4 hours. The reaction solution was washed with water and concentrated. Then the concentrate was crystallized from ethyl acetate to give 0.49 g (yield: 43%) of the desired compound 34.

$^1$H NMR spectrum ($\delta$, CDCl$_3$): 2.8 (3H, d, J=4.5 Hz), 3.0 (2H, dt, J=3 Hz, 6 Hz), 3.6 (2H, t, J=6 Hz), 4.0 (2H, s), 6.4 (1H, br), 6.9–7.4 (10H, m).

EXAMPLE 26

Synthesis of the compound 36

In methylene chloride were dissolved 0.32 g of the compound 29 and 0.11 ml of N,N-dimethylethylenediamine. Thereto was added 0.23 g of w.s.c and the reaction was carried out at room temperature for 18 hours. The reaction solution was washed with water and concentrated. The concentrate was crystallized from ethyl acetate to give 80 mg (yield: 20%) of the desired compound 36.

$^1$H NMR spectrum ($\delta$, CDCl$_3$): 2.1 (6H, s), 2.3 (2H, t, J=6 Hz), 3.0 (2H, dt, J=3 Hz, 6 Hz), 3.2 (2H, t, J=6 Hz), 3.5 (2H, t, J=6 Hz), 4.0 (2H, s), 6.5 (1H, br), 6.8–7.4 (10H, m).

EXAMPLE 27

Synthesis of the compound 37

In a mixed solution of 60 ml of methylene chloride and 15 ml of DMF was dissolved 5 g of the compound 29. Thereto were added 2.3 g of 1-hydroxybenzotriazole and 3.4 g of 1,3-dicyclohexylcarbodiimide. The reaction was carried out at room temperature for 30 minutes. Then thereto was added 1.5 ml of 29% aqueous ammonia and the reaction was carried out for 5 hours. The reaction solution was filtrated and the filtrate was diluted with 100 ml of methylene chloride. The solution was washed three times with 30 ml of 5% aqueous solution of sodium bicarbonate, with water, two times with 30 ml of 5% aqueous solution of citric acid and then with water successively. Then the solution was dried over magnesium sulfate and concentrated. Thus 1.4 g of N-(1-methylcarbamoyl)-3-(m-phenoxybenzylidene)-pyrrolidin-2-one was obtained.

In 3 ml of dimethylformamide was dissolved 0.3 g of the above mentioned product. Thereto was added 60 mg of cyanuric chloride in an atmosphere of argon. The reaction was carried out at room temperature for 10 hours. To the reaction solution was added 5 ml of ice water. The mixture was extracted three times with 5 ml of chloroform. After washing with water, the extract was dried over magnesium sulfate. The solvent was distilled away under reduced pressure and the residue was crystallized from methanol to give 60 mg (yield: 21%) of the desired compound 37.

IR spectrum: $\nu_{max}^{KBr}$ cm$^{-1}$ 3450, 2950, 2240, 1690, 1660, 1590, 1570, 1490, 1260.

$^1$H NMR spectrum ($\delta$, CDCl$_3$): 3.1 (2H, dt, J=3 Hz, 6 Hz), 3.6 (2H, t, J=6 Hz), 4.4 (2H, s), 6.95–7.35 (10H, m).

EXAMPLE 28

Synthesis of the compound 38

In anhydrous ether was dissolved 1.8 g of N,N-dimethylhydrazine in an atmosphere of argon. Thereto was added 4.2 ml of triethylamine. The reaction solution was cooled to −78° C. Thereto was added dropwise 7.9 g of 2,4-dibromobutylyl chloride. The temperature was raised slowly to room temperature and the reaction was carried out for 2 hours. After the reaction, water was poured into the reaction solution. The ether layer thereof was washed with saturated aqueous solution of sodium bicarbonate and then dried over magnesium sulfate. The solvent was distilled away under reduced pressure without heating to give 2.2 g of N-(N', N'-dimethylamino)-2,4-dibromobutyrylamide.

In 20 ml anhydrous tetrahydrofuran was dissolved 2.2 g of the above mentioned product. Thereto was added 0.34 g of sodium hydride (oiliness, content: 60%) with ice-cooling. After the addition, the reaction was carried out at room temperature for 20 hours. After the reaction, thereto was added water. The solution was extracted with chloroform. The extract was dried over magnesium sulfate and concentrated to give 0.34 g of N-(N',N'-dimethylamino)-3-bromopyrrolidin-2-one.

In anhydrous tetrahydrofuran, 0.34 g of the obtained product and 0.47 g of triphenylphosphine were reacted at 60° C. for 30 hours. After the reaction, the solvent was distilled away under reduced pressure. The residue was dissolved in 1 ml of anhydrous ethanol. Thereto were added 0.20 ml of triethylamine and 0.26 ml of m-phenoxybenzaldehyde. The reaction was carried out at 60° C. for 2 hours. The solvent was distilled away under reduced pressure. The residue was then dissolved in chloroform. The solution was washed with water, dried over magnesium sulfate and concentrated. Then the concentrate was crystallized from ethyl acetate to give 40 mg (yield: 8%) of the desired compound 38.

$^1$H NMR spectrum ($\delta$, CDCl$_3$): 2.8 (6H, s) 3.0 (2H, dt, J=3 Hz, 6 Hz), 3.6 (2H, t, J=6 Hz), 7.0-7.5 (10H, m).

EXAMPLE 29

Synthesis of the compound 39

In 5.7 ml of dry dimethylformamide was dissolved 0.85 g of the compound 27. Thereto was added 0.53 g of potassium phtalimide. The reaction was carried out at 90° C. for 7 hours. Thereto was added 8.6 ml of chloroform and the reaction solution was poured into 28 ml of water. The mixture was extracted with chloroform. The organic layer thereof was washed with 6 ml of saturated sodium bicarbonate and then with water, and concentrated. The residue was dissolved in 20 ml of methanol. Thereto was added 0.08 ml of hydrazine monohydrate followed by refluxing for 1 hour. After cooling, thereto was added 5 ml of water. The solvent was distilsed away under reduced pressure. Thereto was added 5 ml of concentrated hydrochloric acid followed by refluxing for 1 hour. The reaction solution was cooled to 0° C., filtrated and concentrated. The residue was dissolved in 10 ml of water and the solution was filtrated. The filtrate was basified with sodium hydroxide and extracted with chloroform. The extract was dried over magnesium sulfate and then concentrated. The residue was dissolved in methanol. Thereto was added 0.5 ml of concentrated hydrochloric acid. After cooling, there precipitated 0.25 g (yield: 44%) of the crystalline of the desired compound 39.

$^1$H NMR spectrum ($\delta$, CDCl$_3$-DMSO-d$_6$): 2.9 (2H, t, J=6 Hz), 3.0 (2H, dt, J=3 Hz, 6 Hz), 3.5 (4H, t, J=6 Hz, t, J=6 Hz), 6.9-7.35 (10H, m).

EXAMPLE 30

Synthesis of the compound 40

In 5 ml of water were dissolved 0.15 g of dimethylamine hydrochloride and 0.32 g of sodium bicarbonate. Thereto was gradually added 10 ml of a solution containing 0.49 g of the compound 27 in methanol. After the addition, the mixture was refluxed for 4 hours. After cooling, the reaction solution was filtrated and methanol was distilled away under reduced pressure. Then the residue was extracted with chloroform and the extract was concentrated. The residue was crystallized from methanol to give 10 mg (yield: 2%) of the desired compound 40.

$^1$H NMR spectrum ($\delta$, CDCl$_3$): 2.25 (6H, s), 2.5 (2H, t, J=6 Hz), 3.0 (2H, dt, J=3 Hz, 6 Hz), 3.5 (4H, t, t), 6.9-7.35 (10H, m).

EXAMPLE 31

Synthesis of the compound 41

In 3.7 ml of acetic anhydride, 2.59 g of the compound 1 was refluxed for 4 hours. After gradually cooling to room temperature, the mixture was cooled to 10° C. and filtrated. The filtrate was washed five times with 175 ml of ether to give 1.85 g (61%) of the desired compound 41.

$^1$H NMR spectrum: 2.6 (3H, s), 3.0 (2H, dt, J=3 Hz, 6 Hz), 3.8 (2H, t, J=6 Hz), 6.9-7.5 (10H, m).

EXAMPLE 32

Synthesis of the compound 42

In methylene chloride were dissolved 2.2 g (8.1 mmole) of the compound 1 and 0.82 g (8.1 mmole) of triethylamine. Thereto was added 1.14 g (8.1 mmole) of benzoyl chloride with stirring on an ice bath. The reaction was carried out at room temperature overnight. The reaction solution was washed with water and the solvent was distilled away under reduced pressure. The crude product was purified by silica gel column chromatography (eluting solvent: chloroform) to give 1.6 g (yield: 52%) of the desired compound 42.

$^1$H NMR spectrum ($\delta$, CDCl$_3$): 3.10 (2H, dt, J=3 Hz, 7.5 Hz), 4.00 (2H, t, J=7.5 Hz), 7.00-7.70 (15H, m).

EXAMPLE 33

Synthesis of the compound 43

The procedure of Example 32 was repeated except for using p-methoxybenzoyl chloride instead of benzoyl chloride in Example 32 to give 0.7 g (yield: 35%) of the desired compound 43.

$^1$H NMR spectrum ($\delta$, CDCl$_3$): 3.05 (2H, dt, J=3 Hz, 6 Hz), 3.80 (3H, s), 3.95 (2H, t, J=7.5 Hz), 6.85-7.45 (12H, m) 7.60 (2H, d, J=9 Hz)

EXAMPLE 34

Synthesis of the compound 45

To 0.12 g of sodium hydride (oiliness, content: 60%) was added dimethylformamide on an ice bath in an atmosphere of argon to give a suspension. Thereto was added dropwise a solution containing 0.82 g of the compound 1 in dimethylformamide and successively 0.29 ml of bromoacetone. Then the reaction was carried out at room temperature for 18 hours. After cooling, water was poured into the reaction solution and the solution was extracted with chloroform. After washing with water, the extract was dried over magnesium sulfate and concentrated to give 0.12 g (yield: 12%) of the desired compound 45.

$^1$H NMR spectrum: 2.0 (3H, s), 3.0 (2H, dt, J=3 Hz, 6 Hz), 3.5 (2H, t, J=6 Hz), 4.2 (2H, s), 6.8-7.4 (10H, m).

EXAMPLE 35

Synthesis of the compound 46

The procedure of Example 14 was repeated except for using (N-phenyl-2-oxopyrrolid-3-yl)-triphenylphosphonium bromide instead of (N-methoxy-2-oxopyrrolid-3-yl)triphenylphosphonium bromide in Example 14 to give 60 mg (yield: 3.4%) of the desired compound 46.

$^1$H NMR spectrum ($\delta$, CDCl$_3$): 3.10 (2H, dt, J=3 Hz, 6 Hz), 3.93 (2H, t, J=7.5 Hz), 6.80-7.82 (15H, m).

EXAMPLE 36

Synthesis of the compound 47

The procedure of Example 10 was repeated except for using 2,4-difluoroaniline instead of cyclopropylamine in Example 10 to give 2.95 g (yield: 47%) of the desired compound 47.

$^1$H NMR spectrum ($\delta$, CDCl$_3$): 3.15 (2H, dt, J=3 Hz, 6 Hz), 3.90 (2H, t, J=7 Hz), 6.80-7.55 (13H, m).

EXAMPLE 37

Synthesis of the compound 48

The procedure of Example 7 was repeated except for using benzyl bromide instead of ethyl iodide in Example 7. The crude product was purified by silica gel column chromatography (eluting solvent: chloroform) to give 1.1 g (yield: 38%) of the desired compound 48.

$^1$H NMR spectrum ($\delta$, CDCl$_3$): 3.00 (2H, dt, J=3 Hz, 6 Hz), 3.38 (2H, t, J=6 Hz), 4.62 (2H, s), 6.95-7.48 (15H, m).

EXAMPLE 38

Synthesis of the compound 51

The procedure of Example 7 was repeated except for using phenethyl bromide instead of ethyl iodide in Example 7. The crude product was purified by silica gel column chromatography (eluting solvent: chloroform) to give 0.1 g (yield: 16%) of the desired compound 51.

$^1$H NMR spectrum ($\delta$, CDCl$_3$): 2.82-2.98 (4H), 3.35 (2H, t, J=6 Hz), 3.70 (2H, dt, J=7.5 Hz), 6.90-7.45 (15H, m).

EXAMPLE 39

Synthesis of the compound 52

In 100 ml of dry THF was suspended 4.8 g of 60% sodium hydride (oiliness) in an atmosphere of nitrogen followed by cooling on an ice bath. To the resultant cooled solution was gradually added a solution containing 7.0 ml of m-phenoxybenzaldehyde and 5.6 g of 1-acetyl-5-methyl-2-pyrrolidone dissolved in 300 ml of dry THF. After the addition, the obtained suspension was warmed to room temperature and the reaction was carried out for 16 hours with stirring. After the reaction, the reaction solution was cooled and thereto was added gradually 40 ml of methanol and then 6N sulfuric acid to acidify the solution. The solution was extracted with chloroform and the extract was dried. Then the solvent was concentrated under reduced pressure. The obtained residue was subjected to column chromatography with silica gel as a carrier and eluted with chloroform. The fraction containing the desired compound was collected and the solvent was distilled away. The residue was recrystallized from a mixed solvent of chloroform and hexane to give 8.8 g (yield: 78%) of the desired compound 52.

$^1$H NMR spectrum ($\delta$, CDCl$_3$): 1.29 (d, J=6 Hz, 3H), 2.57 (m, 1H), 3.22 (m, 1H), 3.86 (m, 1H), 6.76-7.57 (m, 11H).

EXAMPLE 40

Synthesis of the compound 53

The procedure of Example 7 was repeated except for using 4.5 g of the compound 60 instead of the compound 1 to give 3.5 g (yield: 71%) of the desired compound 53.

$^1$H NMR spectrum ($\delta$, CDCl$_3$): 1.12 (t, J=7 Hz, 3H), 1.23 (J=5 Hz, 3H), 1.14-2.47 (m, 2H), 2.80-3.90 (m, 3H), 6.63-7.64 (m, 10H).

EXAMPLE 41

Synthesis of the compound 54

In 200 ml of acetic acid were dissolved 12.9 g of 1-ethylmaleimide and 26.2 g of triphenylphosphine. The solution was heated to 90° C. on an oil bath and the reaction was carried out with stirring for 40 minutes. After the reaction, 1 l of ethyl ether was added to the cooled reaction solution and the mixture was stirred enough. The resultant precipitate was collected by the filtration to give 27 g (yield: 66%) of 3-triphenylphospholanyridene-1-ethylsuccinimide.

In 100 ml of DMSO were dissolved 27 g of the ylide and 12 ml of m-phenoxybenzaldehyde. The resultant solution was heated to 80° C. on an oil bath and the reaction was carried out with stirring for 5 hours. After the reaction, 1 l of water was added to the cooled reaction solution and the solution was extracted with chloroform. Then the solvent was distilled away under reduced pressure and the residue was crystallized from ethanol to give 17 g (yield: 83%) of 1-ethyl-3-(m-phenoxybenzylidene)succinimide.

In a mixed solvent of 200 ml of THF and 300 ml of ethanol was dissolved 10 g of 1-ethyl-3-(m-phenoxybenzylidene)-succinimide. After cooling on an ice bath, 12.3 g of sodium borohydride was added to the resultant solution and the mixture was stirred for 1 hour. During the stirring, thereto was added 5 drops of ethanol containing 2N hydrochloride (gas) every 15 minutes. After the reaction, the reaction mixture was poured into ice water and extracted with chloroform. After drying chloroform layer, the solvent was distilled away under reduced pressure. To the residue were added ethyl acetate and hexane to carry out the crystallization. Thus 4.1 g (yield: 45%) of the desired compound 54 was given.

$^1$H NMR spectrum ($\delta$, CDCl$_3$): 1.16 (t, J=7 Hz, 3H), 2.56-2.96 (m, 1H), 3.00-3.80 (m, 3H), 5.26 (br, 1H), 6.80-7.53 (m, 10H)

EXAMPLE 42

Synthesis of the compound 56

The procedure of Example 41 was repeated except for using 10 g of maleimide instead of 1-ethylmaleimide for reacting with 26.2 g of triphenylphosphine to give 32 g (yield: 89%) of 3-triphenylphospholanylidenesuccinimide.

In the same way as in Example 41, 32 g of the resultant ylide and 15 ml of m-phenoxybenzaldehyde were reacted to give 15 g (yield: 60%) of 3-(m-phenoxybenzylidene)succinimide.

In the same way as in Example 41, 2.0 g of 3-(m-phenoxybenzylidine)succinimide was reduced with sodium borohydride. After the reaction, the reaction mixture was adjusted to pH 3 by adding ethanol containing 2N-hydrochloride (gas). The mixture was stirred on an ice bath for 1 hour. After stirring, the mixture was poured into cold water and extracted with chloroform. The chloroform layer was dried and then the solvent was distilled away under reduced pressure to give 1.7 g (yield 77%) of the desired compound 56.

$^1$H NMR spectrum ($\delta$, CDCl$_3$): 1.22 (t, J=7 Hz, 3H). 2.80—3.45 (m, 2H), 3.57 (q, J=7 Hz, 2H), 5.10 (m, 1H), 6.84–7.52 (m, 10H).

EXAMPLE 43

Synthesis of the compound 57

In the same way as in the above mentioned Example 41, 10 g of 1-ethyl-3-(m-phenoxybenzylidene)succinimide was reduced with sodium borohydride. After the reaction, the reaction mixture was adjusted to pH 3 by adding ethanol containing 2N-hydrochloride (gas). The mixture was stirred on an ice bath for 1 hour. After the reaction, the resultant mixture was poured into cold water and extracted with chloroform. The chloroform layer was dried and then the solvent was distilled away under reduced pressure to give 4.0 g (yield: 36%) of the desired compound 57.

$^1$H NMR spectrum ($\delta$ CDCl$_3$): 1.22 (t, J=7 Hz, 3H), 2.82–3.10 (m, 1H), 3.13–3.86 (m, 3H), 3.42 (q, J=7 Hz, 2H), 5.14 (dd, 6.2 Hz, 1H), 6.76–7.53 (m, 10H).

EXAMPLE 44

Synthesis of the compound 58

A solution containing 2.8 ml of diisopropylamine in dry THF was cooled to $-10°$ C. Thereto was added 12.5 ml of a solution containing 1.6M of n-butyl lithium in hexane in an atmosphere of nitrogen. After 30 minutes, the resultant solution was cooled to $-70°$ C. and thereto was added 3.1 g 5-(hydroxylmethyl)-2-pyrrolidinone-O,N-acetonide. The mixture was stirred for 1 hour. Successively thereto was added 3.5 ml of m-phenoxybenzaldehyde. The reaction was carried out from $-70°$ C. to room temperature for 18 hours. After the reaction, water was added to the reaction solution and the solution was extracted with chloroform. The solvent was distilled away under the reduced pressure. The residue was subjected to column chromatography with silica gel as a carrier and eluted with chloroform to give 3.0 g (yield: 70%) of 3-(1'-hydroxybenzyl)-5-(hydroxymethyl)-2-pyrrolidinone-O,N-acetonide.

In 100 ml of benzene was dissolved 3.0 g of the resultant compound. Thereto was added 3.0 g of p-toluenesulfonic acid. The mixture was heated under reflux for 3 days. After the reaction, the solvent was distilled away under reduced pressure. The residue was subjected to column chromatography with silica gel as a carrier and eluted with chloroform containing 2% of methanol to give 0.8 g (yield: 32%) of the desired compound 58.

$^1$H NMR spectrum ($\delta$, CDCl$_3$): 2.69 (d, J=18 Hz, 1H), 3.04 (dd, J=18, 6 Hz, 1H), 3.45 (d, J=11 Hz, 1H), 3.71 (d, J=11 Hz, 1H), 3.87 (br, 1H), 6.80–7.40 (m, 11H).

EXAMPLE 45

Synthesis of the compound 59

In 50 ml of ethanol were dissolved 0.72 g of the compound 56 and 2.0 ml of pyrrolidine. The resultant solution was refluxed on an oil bath for 24 hours. After the reaction, the solution was evaporated to dryness under reduced pressure. The residue was subjected to column chromatography with silica gel as a carrier and eluted with chloroform. The fraction containing the desired compound was collected. The solvent was evaporated to dryness to give 0.18 g (yield: 23%) of the desired compound 59.

$^1$H NMR spectrum ($\delta$, CDCl$_3$): 1.60–2.00 (m, 4H), 2.40–2.80 (m, 5H), 2.87–3.20 (m, 1H), 4.78 (dd, J=6, 3 Hz, 1H), 6.76–7.53 (m, 10H).

EXAMPLE 46

Synthesis of the compound 60

The procedure for the reaction of Example 39 was repeated except for using 5.8 g of 1-acetyl-4-methyl-2-pyrrolidone instead of 1-acetyl-5-methyl-2-pyrrolidone. Then the purification was carried out using column chromatography with silica gel as a carrier and the elution was carried out with chloroform to give 2.6 g (yield: 23%) of the desired compound 60.

$^1$H NMR spectrum ($\delta$, CDCl$_3$): 1.20 (d, J=7 Hz, 3H), 3.06 (dd, J=9, 1 Hz, 1H), 3.23–3.80 (m, 1H), 3.61 (dd, J=9, 1 Hz, 1H), 6.74–7.54 (m, 10H), 7.67 (br, 1H).

EXAMPLE 47

Synthesis of the compound 61

The procedure of Example 7 was carried out except for using the compound 60 instead of the compound 1 to give the desired compound 61 (yield: 85%).

$^1$H NMR spectrum ($\delta$, CDCl$_3$): 1.18 (t, J=7 Hz, 3H), 1.19 (d, J=7 Hz, 3H), 2.97 (dd, J=9, 1Hz, 1H), 3.22–3.80 (m, 1H), 3.48 (q, J=7 Hz, 2H), 3.57 (dd, J=9, 1 Hz, 1H), 6.80–7.54 (m, 10H).

EXAMPLE 48

Synthesis of the compound 62

The procedure of Example 1 was repeated except for using 1-acetyl-4-phenyl-2-pyrrolidone instead of 1-acetyl-2-pyrrolidone to give the desired compound 62 (yield: 21%).

$^1$H NMR spectrum ($\delta$, CDCl$_3$): 3.28 (dd, J=7 Hz, 1 Hz, 1H), 3.85 (dd, J=7 Hz, 1 Hz, 1H), 4.35 (td, J=7, 2 Hz, 1H), 6.0–7.44 (m, 15H), 7.53 (d, J=2 Hz, 1H).

EXAMPLE 49

Synthesis of the compound 63

In 300 ml of dry ether was dissolved 6.0 g of the compound 1 in an atmosphere of nitrogen. The solution was cooled on an ice bath. To this cooled solution was gradually added 4.3 g of lithium aluminum hydride. After the addition, the obtained suspension was heated under reflux with stirring on an oil bath for 8 hours. After the reaction, the reaction solution was cooled and thereto was gradually added 50 ml of cold water. The solution was extracted three times with 100 ml of ether. The extract was filtrated and distilled away under reduced pressure to give 3.5 g (yield: 60%) of the desired compound.

$^1$H NMR spectrum ($\delta$, CDCl$_3$): 2.63 (td, J=6.1 Hz, 2H), 3.14 (t, J=6 Hz, 2H), 3.67 (br, 2H), 6.30–6.50 (m, 1H), 6.77–7.53 (m, 9H).

EXAMPLE 50

Synthesis of the compound 64

In 300 ml of dry ether was dissolved 6.0 g of the compound 1 in an atmosphere of nitrogen. The solution was cooled on an ice bath. To the resultant cooled solution was gradually added 4.3 g of lithium aluminum hydride. After the addition, the obtained suspension was heated under reflux with stirring on an oil bath for 8 hours. After the reaction, the reaction solution was cooled and thereto was gradually added 50 ml of cold water. The solution was extracted three times with 100 ml of ether. The extract was filtrated and the filtrate was extracted with 50 ml of 2N hydrochloric acid. The extract was cooled on an ice bath and the formed solid was filtrated to give 3.4 g (yield: 52%) of the desired compound 64.

IR spectrum: $\nu_{max}^{KBr}$cm$^{-1}$; 3470, 2840, 2746, 2595, 2477, 1597, 1580, 1493, 1489, 1273, 1218, 807, 792, 714.

$^1$H NMR spectrum ($\delta$, CDCl$_3$): 2.92 (td, J=7 Hz, 1 Hz, 2H), 3.49 (t, J=7 Hz, 2H), 4.19 (m, 2H), 6.54 (m, 1H), 6.77-7.54 (m, 9H).

EXAMPLE 51

Synthesis of the compound 65

The procedure of Example 52 was repeated except for using the compound 9 instead of the compound 10 to give the desired compound 65 (yield: 60%).

$^1$H NMR spectrum ($\delta$, CDCl$_3$): 2.16 (s, 3H), 2.48 (br, 4H), 3.10 (br, 2H), 6.00-6.20 (m, 1H), 6.55-7.32 (m, 9H).

EXAMPLE 52

Synthesis of the compound 66

In 300 ml of dry ether was dissolved 7.0 g of the compound 10 in an atmosphere of nitrogen. The solution was cooled on an ice bath. To the resultant cooled solution was gradually added 4.5 g of lithium aluminum hydride. After the addition, the obtained suspension was heated under reflux with stirring on an oil bath for 8 hours. After the reaction, the reaction solution was cooled and thereto was gradually added 50 ml of cold water. The solution was extracted three times with 100 ml of ether. The extract was filtrated and the filtrate was extracted with 50 ml of 2N hydrochloric acid. The extract was cooled on an ice bath and neutralized with potassium carbonate. Then the resultant solution was extracted four times with 100 ml of ether. The solvent was evaporated under reduced pressure. The obtained oily product was subjected to column chromatography with silica gel as a carrier and eluted with chloroform to give 4.4 g (yield: 66%) of the desired compound 66.

IR spectrum: $\nu_{max}^{KBr}$cm$^{-1}$; 3000, 2825, 1608, 1588, 1502, 1267, 1233, 706.

$^1$H NMR spectrum ($\delta$, CDCl$_3$): 1.15 (t, J=7 Hz, 3H), 2.53 (q, J=7 Hz, 2H), 2.72 (m, 4H), 3.32 (m, 2H), 6.29 (m, 1H), 6.70-7.50 (m, 9H).

EXAMPLE 53

Synthesis of the compound 68

The procedure of Example 11 was repeated except for using the compound 12 instead of the compound 2 in Example 11 to give 50 mg (yield: 4.4%) of the desired compound 68.

$^1$H NMR spectrum ($\delta$, CDCl$_3$): 0.90 (3H, t, J=6 Hz), 1.45 (4H, m), 2.50 (2H, t, J=7.5 Hz), 2.70 (4H, s), 3.35 (2H, s), 6.30 (1H, s), 6.75-7.45 (9H, m).

EXAMPLE 54

Synthesis of the compound 69

In a similar manner as Example 7 except for using allyl bromide instead of ethyl iodide in Example 7, N-allyl-3-(m-phenoxybenzylidene)-pyrrolidin-2-one was obtained. The procedure of Example 11 was repeated except for using 3.9 g of the resultant compound as a starting material instead of the compound 2 in Example 11 to give 1.5 g (yield: 40%) of the desired compound 69.

$^1$H NMR spectrum ($\delta$, CDCl$_3$): 2.66-2.75 (4H, m), 3.15 (2H, dd, J=6.5 Hz, 13.2 Hz), 3.32 (2H, s), 5.12 (1H, d, J=11 Hz), 5.22 (1H, dd, J=1 Hz, 17 Hz), 5.9 (1H, m), 6.29 (1H, s), 6.75-7.45 (9H, m).

EXAMPLE 55

Synthesis of the compound 70

The procedure of Example 11 was repeated except for using the compound 24 instead of the compound 2 in Example 11 to give 0.12 g (yield: 4%) of the desired compound 70.

$^1$H NMR spectrum ($\delta$, CDCl$_3$): 1.6 (6H, m), 2.7 (6H, m), 3.4 (2H, s), 3.5 (2H, t, J=4.5 Hz), 3.8 (2H, m), 4.6 (1H, s), 6.30 (1H, s), 6.8-7.4 (9H, m).

EXAMPLE 56

Synthesis of the compound 71

The procedure of Example 11 was repeated except for using the compound 25 instead of the compound 2 in Example 11 to give 100 mg (yield: 10%) of the desired compound 71.

$^1$H NMR spectrum ($\delta$, CDCl$_3$): 2.67 (4H, m), 2.78 (2H, t, J=6 Hz), 3.38 (2H, s), 3.67 (2H, t, J=6 Hz), 6.29 (1H, s), 6.82-7.35 (9H, m).

EXAMPLE 57

Synthesis of the compound 72

In 10 ml of dry ether was dissolved 0.3 g of the compound 64. To the resultant solution were added 0.1 ml of ethyl chlorocarbonate and 0.28 ml of triethylamine. The mixture was stirred at room temperature for 18 hours. After the reaction, the reaction solution was washed with water and dried over sodium sulfate. Then the solvent was distilled away. The residue was subjected to column chromatography with silica gel as a carrier and eluted with chloroform to give 0.3 g (yield: 94%) of the desired compound 72.

$^1$H NMR spectrum ($\delta$, CDCl$_3$): 1.28 (t, J=7 Hz, 3H), 2.81 (t, J=7 Hz, 2H), 3.60 (t, J=7 Hz, 2H), 4.18 (q, J=7 Hz, 2H), 4.21 (br, 2H), 6.28-6.50 (m, 1H), 6.90-7.64 (m, 9H).

EXAMPLE 58

Synthesis of the compound 73

The procedure of Example 11 was repeated except for using the compound 1 instead of the compound 2 in Example 11 to give 2-(m-phenoxybenzylidene)-pyrrolidine. This was dissolved in ether and the solution was extracted twice with 2N hydrochloric acid. The extract was cooled to crystallize 2-(m-phenoxybenzylidene)-pyrrolidine hydrochloride.

In water was dissolved 0.49 g of the resultant hydrochloride salt. The solution was adjusted from pH 2.8 to pH 3.2 with 50% aqueous solution of potassium hydroxide. Thereto was added an aqueous solution containing 1.4 g of potassium cyanate as a whole amount. After the addition, the reaction was carried out at 20° C. for 18 hours. Water was added to the reaction solution and the solution was extracted with chloroform. The extract was concentrated and the concentrate was crystallized from methanol to give 0.33 g (yield: 65%) of the desired compound 73.

$^1$H NMR spectrum ($\delta$, CDCl$_3$): 2.8 (2H, dt, J=3 Hz, 6 Hz), 2.6 (2H, t, J=7.5 Hz), 4.2 (2H, s), 4.6 (2H, br), 6.4 (1H, s), 6.87–7.4 (9H, m).

EXAMPLE 59

Synthesis of the compound 74

In 5 ml of pyridine was dissolved 0.3 g of the compound 64. To the resultant solution was added 0.1 ml of acetic anhydride. The mixture was stirred at room temperature for 2 hours and then the reaction was carried out at 70° C. on an oil bath for 2 hours. The cooled reaction solution was poured into cold water and extracted with ether. The extract was washed with 0.1N hydrochloric acid and then dried over sodium sulfate. The solvent was distilled away under reduced pressure. The residue was subjected to column chromatography with silica gel as a carrier and eluted with chloroform. The fraction containing the desired compound was collected and the solvent was removed to give 0.1 g (yield: 34%) of the desired compound 74.

$^1$H NMR spectrum ($\delta$, CDCl$_3$): 2.06 (s, 3H), 2.88 (t, J=7 Hz, 2H), 3.50–3.83 (m, 2H), 4.29 (br, 2H), 6.36–6.56 (m, 1H), 6.75–7.55 (m, 9H).

EXAMPLE 60

Synthesis of the compound 75

The procedure of Example 52 was repeated except for using the compound 53 instead of the compound 10 to give the desired compound 75 (yield: 18%).

$^1$H NMR spectrum ($\delta$, CDCl$_3$): 1.14 (t, J=7 Hz, 3H), 1.17 (d, J=7 Hz, 3H), 1.87–2.30 (m, 2H), 2.33–3.18 (m, 4H), 3.67–4.00 (m, 2H), 6.13–6.37 (m, 1H), 6.67–7.50 (m, 9H)

EXAMPLE 61

Synthesis of the compound 76

The procedure of Example 52 was repeated except for using the compound 61 instead of the compound 10 to give the desired compound 76 (yield: 38%).

$^1$H NMR spectrum ($\delta$, CDCl$_3$): 1.60 (d, J=7 Hz, 3H), 1.13 (t, J=7 Hz, 3H), 1.92–2.20 (m, 1H), 2.30 (m, 2H), 2.52 (q, J=7 Hz, 2H), 3.31 (m, 2H), 6.20–6.40 (m, 1H), 6.76–7.54 (m, 9H).

EXAMPLE 62

Synthesis of the compound 77

In 100 ml of dry THF was dissolved 6.0 g of 3-(m-phenoxybenzylidene)-1-pyrroline. After cooling to −30° C., thereto was added 10 ml of a solution of 3N ethylmagnesium bromide in THF. After stirring for 15 minutes, the stirring was continued at room temperature for 2 hours. The reaction solution was poured into 100 ml of cold water containing 10 ml of concentrated aqueous ammonia and the mixture was extracted with dichloromethane. After the solvent was distilled away, the residue was subjected to column chromatography with silica gel as a carrier and eluted with chloroform to give 2.4 g (yield: 39%) of the desired compound 77.

$^1$H NMR spectrum ($\delta$, CDCl$_3$): 1.03 (t, J=7 Hz, 3H), 1.23–2.11 (m, 2H), 2.50–2.80 (m, 2H), 2.75–3.40 (m, 2H), 3.46–3.73 (m, 1H), 6.17–6.37 (m, 1H), 6.63–7.54 (m, 9H).

EXAMPLE 63

Synthesis of the compound 78

In dry ether was dissolved 0.57 g of the compound 80. Thereto was added 0.34 g of lithium aluminum hydride. The mixture was refluxed with stirring on an oil bath for 6 hours. After the reaction, cold water was added to the cooled mixed solution. The resultant precipitate was filtered and the mother liquor was extracted with ether. The extract was evaporated to dryness under reduced pressure. The residue was subjected to column chromatography with neutral alumina as a carrier and eluted with chloroform to give 0.4 g (yield: 74%) of the desired compound 78.

$^1$H NMR spectrum ($\delta$, CDCl$_3$): 0.90 (t, J=7 Hz, 3H), 1.13 (t, J=7 Hz, 3H), 1.81 (qd, 7, 4 Hz, 2H), 1.97–2.38 (m, 2H), 2.40–3.10 (m, 4H), 3.15–3.45 (m, 1H), 6.10–6.33 (m, 1H), 6.75–7.50 (m, 9H).

EXAMPLE 64

Synthesis of the compound 79

In a similar manner as Example 62 except for using 18 ml of a solution of 1.6M n-butyllithium in hexane instead of 10 ml of the solution of 3N ethyl magnesiumbromide in THF for reacting with 3-(m-phenoxybenzylidene)-1-pyrroline, 3.2 g (yield 44%) of 2-n-butyl-3-(m-phenoxybenzylidene)-pyrrolidine was obtained.

Then in a similar manner as Example 65, except for using 3.2 g of the resultant compound instead of the compound 77 0.8 g (yield: 22%) of 1-acetyl-2-n-butyl-3-(m-phenoxybenzylidene)-pyrrolidine was prepared.

Then the procedure of Example 63 was repeated except for using 0.6 g of the resultant compound instead of the compound 80 to give 0.15 g (yield: 13%) of the desired compound 79.

$^1$H NMR spectrum ($\delta$, CDCl$_3$): 0.92 (t, J=7 Hz, 3H), 1.13 (t, J=7 Hz, 3H), 1.15–1.90 (m, 6H), 2.28 (q, J=7 Hz, 2H), 2.48–3.13 (m, 4H), 3.10–3.42 (m, 1H), 6.10–6.30 (m, 1H), 6.70–7.53 (m, 9H).

EXAMPLE 65

Synthesis of the compound 80

There were mixed 2.1 g of the compound 77 and 10 ml of acetic anhydride, and the mixture was stirred at 110° C. for 2 hours. After cooling the mixture was dissolved in chloroform and washed with saturated sodium bicarbonate. Then the solvent was removed under reduced pressure. The residue was subjected to column chromatography with silica gel as a carrier and eluted with chloroform to give 1.7 g (yield: 71%) of the desired compound 80.

$^1$H NMR spectrum ($\delta$, CDCl$_3$): 0.89 (t, J=7 Hz, 3H), 1.76 (qd, J=7, 6 Hz, 2H), 2.06 (s, 3H), 2.87 (td, J=7, 1 Hz, 2H), 3.62 (t, J=7 Hz, 2H), 4.58 (t, J=6 Hz, 1H), 6.20–6.37 (m, 1H), 6.76–7.50 (m, 9H).

EXAMPLE 66

Synthesis of the compound 82

In an atmosphere of argon there were added methanol, 0.45 g of palladium-carbon and 1.4 g (4.8 mmole) of the compound 10. The mixture was hydrogenated with stirring for 5 hours. After the reaction, the reaction solution was filtrated. Then the solvent was removed under reduced pressure to give 0.87 g (yield: 61%) of the desired compound 82.

$^1$H NMR spectrum (δ, CDCl$_3$): 1.05 (3H, t, J=7.5 Hz), 1.58-2.22 (2H, m), 2.56-2.78 (2H, m), 3.10-3.45 (5H, m), 6.81-7.45 (9H, m).

EXAMPLE 67

Synthesis of the compound 83

The procedure of Example 66 was repeated except for using the compound 66 instead of the compound 10 to give the desired compound 83 (yield: 86%).

$^1$H NMR spectrum (δ, CDCl$_3$): 1.10 (t, J=7 Hz, 3H), 1.21-1.73 (m, 1H), 1.74-2.90 (m, 9H), 3.02-3.63 (m, 1H), 6.72-7.53 (m, 9H).

EXAMPLE 68

Synthesis of the compound 84

The procedure of Example 10 was repeated except for using isopropylamine instead of cyclopropylamine in Example 10 to give N-(2-propyl)-3-(m-phenoxybenzylidene)-pyrrolidin-2-one. The procedure of Example 11 was repeated except for using 0.9 g of the resultant compound as a starting material instead of the compound 2 in Example 11 to give 0.49 g (yield: 58%) of the desired compound 84.

$^1$H NMR spectrum (δ, CDCl$_3$): 2.35 (1H, m), 2.7 (2H, t, J=6 Hz), 2.8 (2H, t, J=7 Hz), 3.38 (2H, s), 6.25 (1H, s), 6.8-7.35 (9H, m).

EXAMPLE 69

Synthesis of the compound 85

The procedure of Example 11 was repeated except for using the compound 11 instead of the compound 2 in Example 11 to give 0.30 g (yield: 22%) of the desired compound 85.

$^1$H NMR spectrum (δ, CDCl$_3$): 0.46 (4H, m), 1.65 (1H, m), 2.66 (2H, t, J=6 Hz), 2.87 (2H, t, J=7 Hz), 3.46 (2H, s), 6.29 (1H, s), 6.78-7.38 (9H, m).

EXAMPLE 70

Synthesis of the compound 86

In toluene, 2.78 g of the compound 1 and 5.10 g of Lowesson's Reagent were refluxed for 1 hour. The reaction solution was poured into water for the crystallization. The crystal was filtrated and was crystallized from benzene to give 1.48 g (yield: 50%) of the desired compound 86.

$^1$H NMR spectrum (δ, CDCl$_3$): 3.2 (2H, dt, J=3 Hz, 6 Hz), 3.7 (2H, t, J=6 Hz), 6.9-7.4 (9H, m), 7.7 (1H, m), 8.4 (1H, br).

EXAMPLE 71

A mixture of 100 g of the compound 1, 55 g of lactose and 41 g of dry potato strach was kneaded with 20 ml of water. The mixture was extruded through 16 mesh screen and dried at 40° C. to give granule. Then the granule was mixed with 4 g of magnesium stearate uniformly and tabletted according to a usual method to give tablets containing 100 mg of the compound 1 per tablet (200 mg).

EXAMPLE 72

The procedure of Example 71 was repeated except for using the compound 10 instead of the compound 1 to give tablets containing 100 mg of the compound 10 per tablet (200 mg).

EXAMPLE 73

The procedure of Example 71 was repeated except for using the compound 64 instead of the compound 1 to give tablets containing 100 mg of the compound 64 per tablet (200 mg).

EXAMPLE 74

The procedure of Example 71 was repeated except for using the compound 67 instead of the compound 1 to give tablets containing 100 mg of the compound 67 per tablet (200 mg).

EXAMPLE 75

The procedure of Example 71 was repeated except for using the compound 75 instead of the compound 1 to give tablets containing 100 mg of the compound 75 per tablet (200 mg).

EXAMPLE 76

After 196 g of granule obtained in the same way as in Example 71 was mixed with 4 g of magnesium sterate, each 200 mg of the mixture was filled into a hard capsule of size 2 to give a hard capsule containing 100 mg of the compound 1 per capsule.

EXAMPLE 77

The procedure of Example 76 was repeated except for using the compound 10 instead of the compound 1 in Example 76 to give a hard capsule containing 100 mg of the compound 10 per capsule.

EXAMPLE 78

The procedure of Example 76 was repeated except for using the compound 64 instead of the compound 1 in Example 76 to give a hard capsule containing 100 mg of the compound 64 per capsule.

EXAMPLE 79

The procedure of Example 76 was repeated except for using the compound 67 instead of the compound 1 in Example 76 to give a hard capsule containing 100 mg of the compound 67 per capsule.

EXAMPLE 80

The procedure of Exmaple 76 was repeated except for using the compound 75 instead of the compound 1 in Example 76 to give a hard capsule containing 100 mg of the compound 75 per capsule.

EXAMPLE 81

| | |
|---|---|
| compound 1 | 10.0 g |
| lactose | 85.0 g |
| crystalline cellulose | 4.5 g |
| magnesium stearate | 1.5 g |

The above-mentioned components were mixed enough to give powder containing 100 mg of the comound 1 per gram.

EXAMPLE 82

The procedure of Example 81 was repeated except for using the compound 10 instead of the compound 1 in Example 81 to give powder containing 100 mg of the compound 10 per gram.

EXAMPLE 83

The procedure of Example 81 was repeated except for using the compound 64 instead of the compound 1 in Example 81 to give powder containing 100 mg of the compound 64 per gram.

EXAMPLE 84

The procedure of Example 81 was repeated except for using the compound 67 instead of the compound 1 in Example 81 to give powder containing 100 mg of the compound 67 per gram.

EXAMPLE 85

The procedure of Example 81 was repeated except for using the compound 75 instead of the compound 1 in Example 81 to give powder containing 100 mg of the compound 75 per gram.

We claim:

1. A phenoxybenzene derivative having the formula (I):

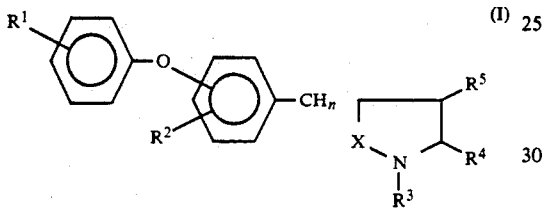

wherein $R^1$ is hydrogen atom; an alkyl group having 1 to 3 carbon atoms; —$OR^6$ wherein $R^6$ is hydrogen atom or an alkyl group having 1 to 3 carbon atoms; or a halogen atom, $R^2$ is hydrogen atom, nitro group or amino group, $R^3$ is hydrogen atom, an alkyl group having 1 to 8 carbon atoms, a cycloalkyl group having 3 to 5 carbon atoms, allyl group, vinyl group or —$(CH_2)n^1R^7$ wherein $R^7$ is

- —$OR^8$ wherein $R^8$ is hydrogen atom, an alkyl group having 1-3 carbon atoms or tetrahydropyranyl group, a halogen atom,
- —$COOR^9$ wherein $R^9$ is hydrogen atom or an alkyl group having 1 to 3 carbon atoms,

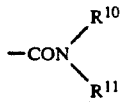

wherein $R^{10}$ and $R^{11}$ are independently hydrogen atom; an alkyl group having 1-3 carbon aroms;

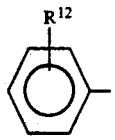

wherein $R^{12}$ is hydrogen atom or —$OR^{13}$ wherein $R^{13}$ is hydrogen atom or an alkyl group having 1 to 3 carbon atoms; or

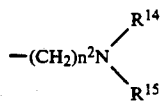

wherein $R^{14}$ and $R^{15}$ are independently hydrogen atom or an alkyl group having 1 to 3 carbon atoms and $n^2$ is an integer of 1 to 3, cyano group,

wherein $R^{16}$ and $R^{17}$ are independently hydrogen atom or an alkyl group having 1 to 3 carbon atoms, —$COR^{18}$ wherein $R^{18}$ is an alkyl group having 1-3 carbon atoms;

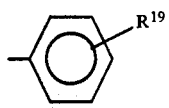

wherein $R^{19}$ is hydrogen atom or —$OR^{20}$ wherein $R^{20}$ is hydrogen atom or an alkyl group having 1 to 3 carbon atoms; or

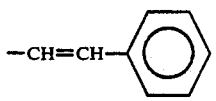

or
a phenyl group having the formula

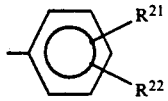

wherein $R^{21}$ and $R^{22}$ are independently hydrogen atom; —$OR^{23}$ and —$OR^{24}$ wherein $R^{23}$ and $R^{24}$ are independently hydrogen atom or an alkyl group having 1 to 3 carbon atoms; or a halogen atom and $n^1$ is an integer of 0 to 4, $R^4$ is hydrogen atom, an alkyl group having 1 to 3 carbon atoms or —$(CH_2)n^3R^{25}$ wherein $R^{25}$ is —$OR^{26}$ wherein $R^{26}$ is hydrogen atom or an alkyl group having 1-3 carbon atoms; or pyrrolidyl group, and $n^3$ is an integer of 0 to 3, $R^5$ is hydrogen atom; an alkyl group having 1 to 3 carbon atoms; or phenyl group, X is

wherein Y is oxygen atom or sulfur atom; or —$CHR^{27}$— wherein $R^{27}$ is hydrogen atom or an alkyl group having 1 to 5 carbon atoms and line ==== means a single bond or a double bond provided that n is 2 in case that the line ==== means a single bond and n is 1 in case that the line ==== means a double bond, or a pharmacologically acceptable salt thereof.

2. A cognition enhancer comprising as an effective ingredient the phenoxybenzene derivative or a pharmacologically acceptable salt thereof of claim 1.

3. An antidepressant comprising as an effective ingredient the phenoxybenzene derivative or a pharmacologically acceptable salt thereof of claim 1.

* * * * *